US012784080B2

(12) United States Patent
Seki et al.

(10) Patent No.: US 12,784,080 B2
(45) Date of Patent: Nov. 3, 2026

(54) PROGRAM, INFORMATION PROCESSING METHOD, INFORMATION PROCESSING DEVICE, AND MODEL GENERATION METHOD

(71) Applicant: TERUMO KABUSHIKI KAISHA, Tokyo (JP)

(72) Inventors: Yusuke Seki, Tokyo (JP); Kohtaroh Kusu, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 198 days.

(21) Appl. No.: 18/191,138

(22) Filed: Mar. 28, 2023

(65) Prior Publication Data

US 2023/0237546 A1 Jul. 27, 2023

Related U.S. Application Data

(63) Continuation of application No. PCT/JP2021/035263, filed on Sep. 27, 2021.

(30) Foreign Application Priority Data

Sep. 28, 2020 (JP) ................................ 2020-162032

(51) Int. Cl.

*G16H 10/60* (2018.01)
*G06Q 30/0283* (2023.01)
*G16H 20/17* (2018.01)

(52) U.S. Cl.

CPC ......... *G06Q 30/0284* (2013.01); *G16H 10/60* (2018.01); *G16H 20/17* (2018.01)

(58) Field of Classification Search

CPC .... G06Q 30/0284; G16H 10/60; G16H 20/17; G16H 20/40; G16H 30/40; G16H 40/20;

(Continued)

(56) References Cited

U.S. PATENT DOCUMENTS 11,110,249 B2 9/2021 Inukai et al.
2003/0083901 A1 * 5/2003 Bosch .................... G16H 40/20 705/2

(Continued)

FOREIGN PATENT DOCUMENTS

JP 2003331058 A 11/2003
JP 2014203275 A 10/2014

(Continued)

OTHER PUBLICATIONS

International Search Report (PCT/ISA/210) with translation and Written Opinion (PCT/ISA/237) mailed on Dec. 7, 2021 by the Japanese Patent Office as the International Searching Authority for International Application No. PCT/JP2021/035263. (9 pages).

*Primary Examiner* — Jason B Dunham
*Assistant Examiner* — Kimberly A. Sass
(74) *Attorney, Agent, or Firm* — Buchanan Ingersoll & Rooney PC

(57) ABSTRACT

A non-transitory computer-readable program, an information processing method, an information processing device, and a model generation method that can predict a time and a fee required for catheter treatment. According to the program, a computer obtains patient information related to a patient for whom catheter treatment is performed, and treatment information related to the catheter treatment to be performed on the patient. Furthermore, the computer outputs a treatment time and a fee required for the catheter treatment based on the obtained patient information and treatment information.

15 Claims, 17 Drawing Sheets

(58) Field of Classification Search
CPC ........ G16H 40/67; G16H 50/20; G16H 50/30; G16H 50/70
USPC .............................................................. 705/2
See application file for complete search history.

(56) References Cited

U.S. PATENT DOCUMENTS

| | | | | |
|---|---|---|---|---|
| 2019/0090954 | A1 | 3/2019 | Kotian et al. | |
| 2019/0304606 | A1* | 10/2019 | Menon | G16H 50/30 |
| 2020/0168334 | A1* | 5/2020 | Mowery | G06N 3/045 |
| 2020/0273569 | A1* | 8/2020 | Sharma | G16H 50/20 |

FOREIGN PATENT DOCUMENTS

| | | | | | |
|---|---|---|---|---|---|
| WO | WO-2012155067 | A1 * | 11/2012 | | G16Z 99/00 |
| WO | WO-2014015100 | A2 * | 1/2014 | | G16H 20/17 |
| WO | 2019150609 | A1 | 8/2019 | | |

* cited by examiner

FIG. 2

| PATIENT ID | PATIENT INFORMATION | | | | | |
|---|---|---|---|---|---|---|
| | AGE | SEX | DIAGNOSIS NAME | RISK FACTOR | PRE-EXISTING DISEASE HISTORY | ... |
| P0001 | 60 | MALE | STABLE ANGINA PECTORIS | HIGH BLOOD PRESSURE | MYOCARDIAL INFARCTION | ... |
| ... | ... | ... | ... | ... | ... | ... |

| TREATMENT INFORMATION | | | | | |
|---|---|---|---|---|---|
| EXECUTION DAY | PERSON IN CHARGE | LESION SITE | LESION PROPERTY | PUNCTURED SITE | CONTRAST AGENT AMOUNT |
| 2020/9/1 | DOCTOR A | RIGHT CORONARY ARTERY | BRANCH LESION | BRACHIAL ARTERY | *** mL |
| ... | ... | ... | ... | ... | ... |

12a

| TREATMENT INFORMATION | | | ... |
|---|---|---|---|
| TREATMENT TIME | FEE | ... | |
| (** HOURS) | (** YEN) | ... | ... |
| ... | ... | ... | ... |

FIG. 6

| CASE ID | PATIENT INFORMATION | | | | | |
|---|---|---|---|---|---|---|
| | AGE | SEX | DIAGNOSIS NAME | RISK FACTOR | PRE-EXISTING DISEASE HISTORY | ... |
| C0001 | 55 | MALE | STABLE ANGINA PECTORIS | HIGH BLOOD PRESSURE | — | ... |
| ... | ... | ... | ... | ... | ... | ... |

| TREATMENT INFORMATION | | | | | |
|---|---|---|---|---|---|
| EXECUTION DAY | PERSON IN CHARGE | LESION SITE | LESION PROPERTY | PUNCTURED SITE | CONTRAST AGENT AMOUNT |
| 2020/4/1 | DOCTOR B | LEFT ANTERIOR DESCENDING CORONARY ARTERY | BRANCH LESION | BRACHIAL ARTERY | *** mL |
| ... | ... | ... | ... | ... | ... |

12b

| TREATMENT INFORMATION | | | ... |
|---|---|---|---|
| TREATMENT TIME | FEE | ... | |
| ** HOURS | ** YEN | ... | ... |
| ... | ... | ... | ... |

FIG. 15A

PATIENT LIST

| DATE | START TIME | END TIME | CATHETER ROOM | PATIENT ID | NAME | AGE | SEX | DIAGNOSIS NAME | TREATMENT CONTENTS | PERSON IN CHARGE |
|---|---|---|---|---|---|---|---|---|---|---|
| 2020/8/24 | 9:30 | (11:30) | A | P0011 | **** | 62 | FEMALE | MYOCARDIAL INFARCTION | PCI, RCA | DOCTOR A |
| 2020/8/24 | (13:30) | (15:00) | A | P1100 | **** | 70 | MALE | ANGINA PECTORIS | PCI, LAD | DOCTOR B |

FIG. 15B

PATIENT ID: P0011 (NAME: ****)

| TIME | PROGRESS | REQUIRED TIME (MINUTES) | PHARMACEUTICAL AGENT / MEDICAL EQUIPMENT | FEE (INSURANCE POINTS) |
|---|---|---|---|---|
| 9:30 | PATIENT ENTERS ROOM | 1 | | |
| 9:31 | MONITOR IS ATTACHED / TIMEOUT / DISINFECT | 4 | | |
| 9:35 | LOCAL ANESTHESIA | 1 | LIDOCAINE | ** |
| ... | ... | ... | ... | ... |
| 9:44 | IVUS | 5 | IVUS | ** |
| 9:49 | RIGHT CAG | 3 | CONTRAST AGENT | ** |
| (9:52) | POBA | 3 | POBA | ** |
| (9:55) | IVUS | 3 | | ** |
| ... | ... | ... | ... | ... |

PROGRAM, INFORMATION PROCESSING METHOD, INFORMATION PROCESSING DEVICE, AND MODEL GENERATION METHOD

CROSS-REFERENCES TO RELATED APPLICATIONS

This application is a continuation of International Application No. PCT/JP2021/035263 filed on Sep. 27, 2021, which claims priority to Japanese Application No. 2020-162032 filed on Sep. 28, 2020, the entire content of both of which is incorporated herein by reference.

TECHNOLOGICAL FIELD

The present disclosure generally relates to a program, an information processing method, an information processing device, and a model generation method.

BACKGROUND DISCUSSION

As minimally invasive treatment for ischemic heart diseases such as angina pectoris or myocardial infarction, intravascular treatment represented by Percutaneous Coronary Intervention (PCI) is performed. PCI (catheter treatment) is a treatment method for inserting a catheter into a blood vessel from a wrist, an elbow, or a grain area of a foot, and expanding a stenosis site of a coronary artery using a balloon and a stent. International Patent Application Publication No. WO 2019/150609 A discloses a technique that assists a surgeon by specifying a shape of a catheter suitable for a state of a blood vessel of a patient, and proposing a catheter having the specified shape before performing catheter treatment.

PCI requires a different treatment time and fee depending on a condition of a patient's blood vessel, equipment in a catheter treatment room, a surgeon's technique, and the like, and therefore has difficulty in performing accurate prediction in advance. Since the treatment time cannot be accurately predicted, it is not possible to efficiently allocate catheter treatment rooms to patients, and it is difficult to improve a utilization rate of the catheter treatment rooms. The technique disclosed in International Patent Application Publication No. WO 2019/150609 A only proposes the shape of the catheter before the operation, and does not predict a time and a fee required for the operation.

SUMMARY

A program or the like that can predict a time and a fee required for catheter treatment.

A non-transitory computer-readable medium storing a program according to one aspect, which when executed by a computer, performs processing comprising: obtaining patient information related to a patient for whom catheter treatment is performed, and treatment information related to the catheter treatment to be performed on the patient; and outputting a treatment time and a fee required for the catheter treatment based on the obtained patient information and the treatment information.

An information processing device according to another aspect comprising: a processor configured to: obtain patient information related to a patient for whom catheter treatment is performed, and treatment information related to the catheter treatment to be performed on the patient; and output a treatment time and a fee required for the catheter treatment based on the obtained patient information and the treatment information.

A model generation method according to a further aspect executed by a computer, the model generation method comprising: obtaining training data obtained by giving a treatment time and a fee required for catheter treatment to patient information related to a patient for whom the catheter treatment has been performed, and treatment information related to the catheter treatment that has been performed on the patient; and generating a learned model that outputs the treatment time and the fee based on the training data when receiving an input of the patient information and the treatment information.

According to one aspect, it is possible to predict a time and a fee required for catheter treatment.

BRIEF DESCRIPTION OF THE DRAWINGS

FIG. 2 is a schematic view illustrating a configuration example of a medical database (DB).

FIG. 6 is a schematic view illustrating a configuration example of a case databased (DB).

FIG. 15A is a schematic view illustrating a screen example.

FIG. 15B is a schematic view illustrating a screen example.

DETAILED DESCRIPTION

Set forth below with reference to the accompanying drawings is a detailed description of embodiments of a program, an information processing method, an information processing device, and a model generation method.

Embodiment 1

An information processing device will be described that predicts a treatment time and a fee required for catheter treatment scheduled to be performed based on patient information related to a patient for whom the catheter treatment is performed and catheter treatment information (referred to simply as treatment information below) related to the catheter treatment scheduled to be performed on the patient, and presents the predicted treatment time and fee to a user (medical worker). Although the present embodiment will describe cardiac catheter treatment that is intravascular treatment as an example, luminal organs that are catheter treatment targets are not limited to blood vessels, and may be other luminal organs such as a bile duct, a pancreatic duct, a bronchus, and an intestine.

Figure 1:
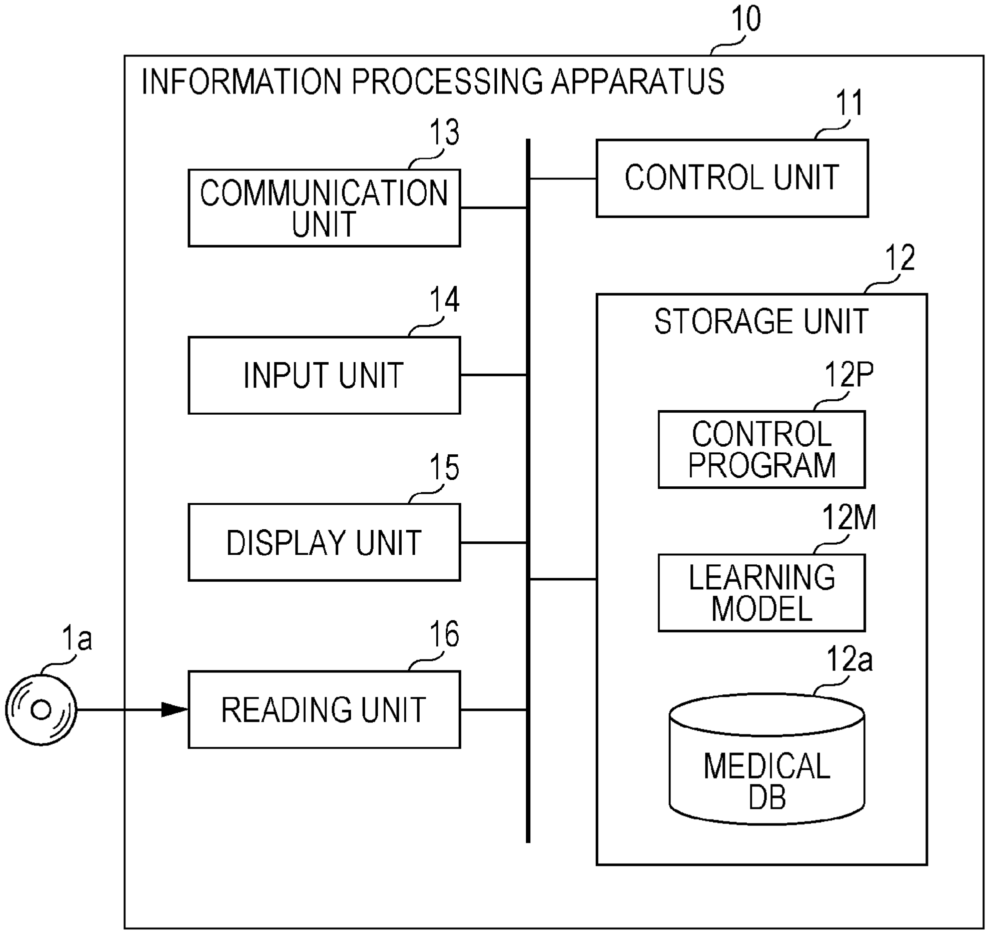
FIG. 1 is a block diagram illustrating a configuration example of an information processing device.

FIG. 1 is a block diagram illustrating a configuration example of the information processing device. An information processing device 10 is a device that can perform various types of processing and transmit and receive various pieces of information, and is, for example, a server computer, a personal computer, or the like. A plurality of the information processing devices 10 may be provided and configured to perform distributed processing, or may be realized by a plurality of virtual machines provided in one device. The information processing device 10 is installed and used in, for example, a medical institution that performs catheter treatment. In a case where the information processing device 10 is configured as a server computer, the information processing device 10 may be a local server installed in a medical institution that performs catheter treatment, or may be a cloud server that is connected by communication via a network such as the Internet.

The information processing device 10 performs processing of outputting a treatment time and a fee required for catheter treatment scheduled to be performed on a patient based on patient information related to the patient for whom the catheter treatment is performed, and treatment information related to a treatment plan of the catheter treatment scheduled to be performed on the patient. More specifically, as will be described later, the information processing device 10 prepares in advance a learning model 12M (see FIG. 3) that performs machine learning for learning predetermined training data, receives an input of the patient information and the treatment information, and outputs the treatment time and the fee. The information processing device 10 inputs patient information and treatment information of a treatment target patient to the learning model 12M, and obtains a treatment time and a fee from the learning model 12M.

More specifically, the information processing device 10 includes a control unit 11, a storage unit 12, a communication unit 13, an input unit 14, a display unit 15, a reading unit 16, and the like, and these units are mutually connected via a bus. The control unit 11 includes one or a plurality of processors such as a Central Processing Unit (CPU), a Micro-Processing Unit (MPU), a Graphics Processing Unit (GPU), or an AI chip (AI semiconductor). The control unit 11 appropriately executes a control program 12P stored in the storage unit 12 to perform various types of information processing, control processing, and the like that the information processing device 10 needs to perform.

The storage unit 12 includes a Random Access Memory (RAM), a flash memory, a hard disk, a Solid State Drive (SSD), and the like. The storage unit 12 stores in advance the control program 12P executed by the control unit 11, various items of data necessary for executing the control program 12P, and the like. Furthermore, the storage unit 12 temporarily stores data and the like generated when the control unit 11 executes the control program 12P. Furthermore, the storage unit 12 stores, for example, the learning model 12M that has learned training data by machine learning. The learning model 12M is a learned model that has learned to output a treatment time and a fee of catheter treatment when receiving an input of patient information of a patient and treatment information related to the catheter treatment scheduled to be performed on the patient. The learning model 12M can be used as a program module that configures artificial intelligence software. The learning model 12M performs a predetermined arithmetic operation on an input value, and outputs an arithmetic operation result, and the storage unit 12 stores data such as a coefficient and a threshold of a function that defines this arithmetic operation as the learning model 12M. Furthermore, the storage unit 12 stores a medical DB 12*a* to be described later. The medical DB 12*a* may be stored in another storage device connected to the information processing device 10, or may be stored in another storage device with which the information processing device 10 can communicate.

The communication unit 13 is a communication module for connecting to a network such as the Internet or a Local Area Network (LAN) by wired communication or wireless communication, and transmits and receives information to and from other devices via the network. The input unit 14 accepts an input of a user's operation, and sends a control signal corresponding to operation contents to the control unit 11. The display unit 15 can be, for example, a liquid crystal display, an organic EL display, or the like, and displays various pieces of information according to an instruction from the control unit 11. The input unit 14 and the display unit 15 may be integrally configured as a touch panel.

The reading unit 16 reads information stored in a portable storage medium 1*a* including a Compact Disc (CD)-ROM, a Digital Versatile Disc (DVD)-ROM, a Universal Serial Bus (USB) memory, a Secure Digital (SD) card, and the like. The control program 12P and various items of data stored in the storage unit 12 may be read from the portable storage medium 1*a* by the control unit 11 via the reading unit 16, and stored in the storage unit 12. Furthermore, the control program 12P and the various items of data stored in the storage unit 12 may be downloaded from another device by the control unit 11 via the communication unit 13, and stored in the storage unit 12.

FIG. 2 is a schematic view illustrating a configuration example of the medical DB 12*a*. The medical DB 12*a* is a database that stores medical data of patients. The medical DB 12*a* illustrated in FIG. 2 includes a patient ID column, a patient information column, a treatment information column, and the like. The patient ID column stores identification information (patient IDs) for identifying each patient. The patient ID may be, for example, a patient registration card number of a patient registration card issued by a medical institution. Each of the patient information column and the treatment information column stores patient information related to a patient, and treatment information related to catheter treatment that has been performed or is scheduled to be performed on the patient in association with a patient ID. The patient information can include, for example, attribute information including an age and a sex of the patient, a diagnosis name, a risk factor (whether or not the patient has a lifestyle disease or the like), symptom information including a pre-existing disease history and indicating a symptom, and the like. Furthermore, the patient information can be a medical record of a patient, and may include a medical history, a concomitant drug, the number of affected blood vessels, a left ventricular ejection fraction, a history of occurrence of a sudden change (myocardial infarction or the like) related to a cardiovascular, various test results such as a blood test and a urine test, a medication history of drugs, and the like. Furthermore, the patient information may include medical images such as X-ray images, ultrasound images, Computed Tomography (CT) images, Magnetic Resonance Imaging (MRI) images, and Positron Emission Tomography (PET) images.

The treatment information is information related to catheter treatment (PCI) that has been performed or is scheduled to be performed on the patient. More specifically, the treatment information can include an execution date of catheter treatment (a date or an execution scheduled day on which the catheter treatment has been or is performed), a person in charge of performing the catheter treatment (medical workers and physicians such as doctors), a position where a lesion such as a plaque exists (referred to as a lesion site below), a property of the lesion, a catheter punctured site, and the like. Furthermore, in addition to the lesion site (e.g., a type of a blood vessel in which the lesion exists) and the property, the treatment information may include information related to the lesion such as a length of the lesion in a longitudinal direction of the blood vessel, a size (area) of the lesion in a cross section of the blood vessel, and the like. Furthermore, the treatment information may include information of a treatment device used for catheter treatment. The treatment device can be, for example, a catheter to be inserted into a blood vessel, a stent for expanding a blood vessel, a balloon, or the like. Note that the treatment device is not limited to the stent and the like, and may include, for example, Rotablator for resecting a lesion. The information related to the treatment device may include catheter information related to the catheter such as a type of a catheter (e.g., product name) that needs to be used. Furthermore, the information related to the treatment device may include stent information related to the stent such as a type of the stent (e.g., product name) that needs to be used, a shape (a diameter and a length), a total number of stents, whether or not a technique is additionally performed before stent implantation and contents of the technique that is additionally performed before the stent implantation, whether or not a technique is additionally performed after stent implantation and contents of the technique that is additionally performed after the stent implantation, and the like. Furthermore, the information related to the treatment device may include balloon information related to a balloon such as a type of a balloon (e.g., product name) that needs to be used, a shape (length), expansion conditions (a maximum expansion pressure, a maximum expansion diameter, an expansion time, and a contraction time required for the balloon to contract after expansion), and the like. Furthermore, the treatment information may include information related to a technique of catheter treatment. The information related to the technique may include, for example, information related to imaging conditions of a fluoroscopic image obtained by visualizing a position of a catheter inserted into a patient's body while PCI is performed. The information related to the imaging conditions may include, for example, a dose of a contrast agent used or scheduled to be used, an imaging time (transillumination time) of the fluoroscopic image, and the like. The fluoroscopic image can be obtained by using, for example, an angiography device that performs angiographic examination, and a position of a catheter is confirmed from the fluoroscopic image.

Furthermore, the treatment information can include a treatment time and a fee of catheter treatment. The treatment time is a treatment time predicted from the patient information and the treatment information and required for the catheter treatment in a case before the catheter treatment is performed, and is a treatment time actually required in a case after the catheter treatment is performed. The fee is the fee predicted from the patient information and the treatment information and required for the catheter treatment in the case before the catheter treatment is performed, and is the fee actually required in the case after the catheter treatment is performed. The fee may be insurance points (medical fee points) in a medical insurance, may be a treatment fee based on the insurance points, or may be a total fee of the treatment fee and labor cost. Regarding the treatment time and the fee, for example, a predicted treatment time and fee are stored in the medical database (DB) 12*a* when predicted from the patient information and the treatment information, and an actual treatment time and fee are stored in the medical DB 12*a* after the catheter treatment is performed. The predicted treatment time and fee and the actual treatment time and fee may be distinguished (i.e., listed separately), and both may be stored in the medical DB 12*a*. In the example illustrated in FIG. 2, the predicted treatment time and fee are stored with parentheses ("(" and ")"). The information processing device 10 predicts the treatment time and the fee required for the catheter treatment according to the patient information and the treatment information using the learning model 12M. A patient identifier (ID) to be stored in the medical DB 12*a* is issued and stored by the control unit 11 every time new patient information is registered. Other information stored in the medical DB 12*a* is stored by the control unit 11 when the control unit 11 obtains the other information via the input unit 14 or the communication unit 13. Storage contents of the medical DB 12*a* is not limited to the example illustrated in FIG. 2, and various pieces of information related to a patient, and various pieces of information related to the treatment performed on the patient and the treatment scheduled to be performed may be stored.

Figure 3:
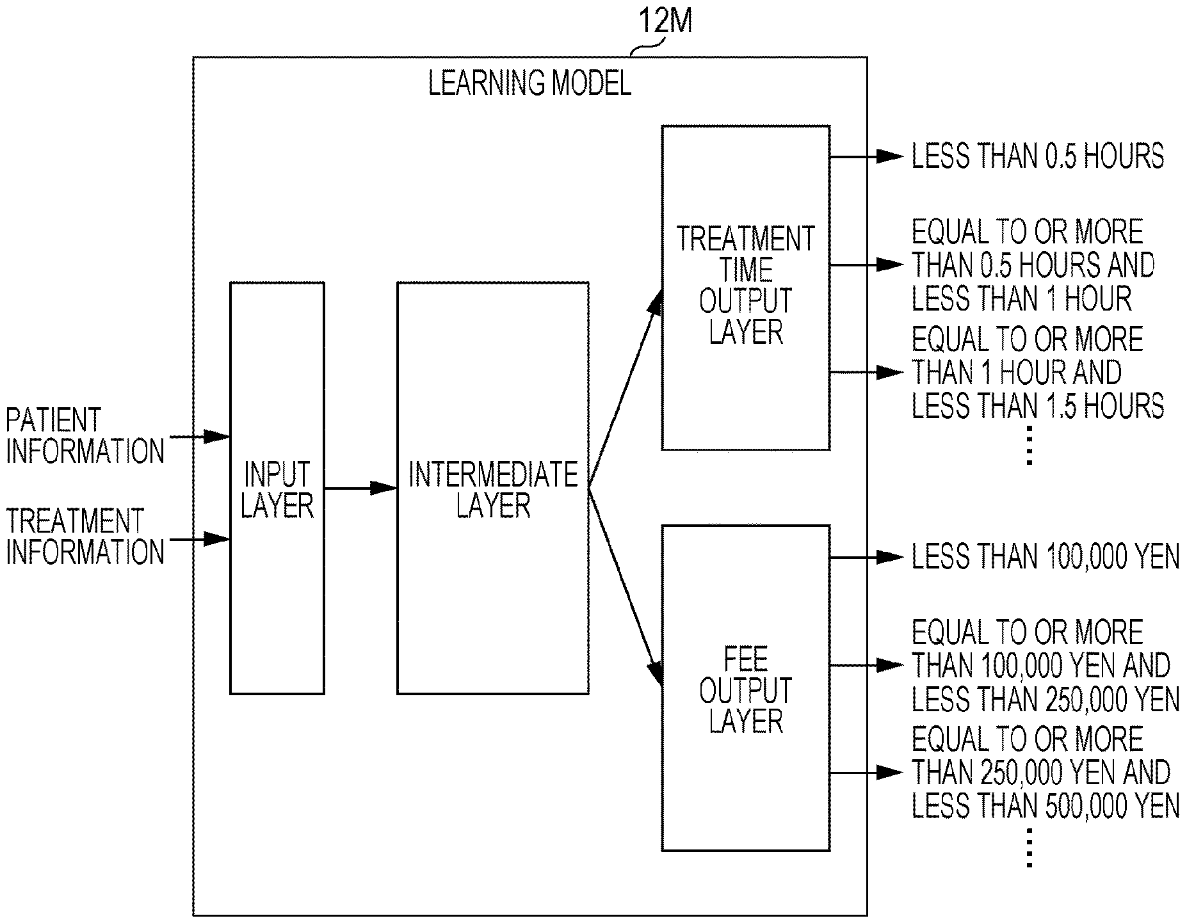
FIG. 3 is a schematic view illustrating a configuration example of a learning model.

FIG. 3 is a schematic view illustrating a configuration example of the learning model 12M. The learning model 12M is a machine learning model that receives an input of the patient information and the treatment information, and outputs the treatment time and the fee required for the catheter treatment related to the treatment information. The learning model 12M can be configured by, for example, a Convolutional Neural Network (CNN) that is a neural network model generated by deep learning. In addition to the CNN, the learning model 12M may be configured using an algorithm such as a Recurrent Neural Network (RNN), a Long Short-Term Memory (LSTM), a Generative Adversarial Network (GAN), a decision tree, a random forest, a Support Vector Machine (SVM), or the like, or may be configured by combining a plurality of algorithms. The information processing device 10 generates the learning model 12M in advance by performing machine learning for learning predetermined training data. Furthermore, the information processing device 10 inputs to the learning model 12M patient information and treatment information of a patient registered in the medical DB 12*a*, and predicts a treatment time and a fee.

The learning model 12M illustrated in FIG. 3 includes an input layer to which patient information and treatment information are input, an output layer that outputs a treatment time and a fee, and an intermediate layer (hidden layer) that extracts a feature amount from the input information. The input layer includes a plurality of input nodes, each input node is associated with information that needs to be input, and each information of the patient information and the treatment information is input to the learning model 12M via the input node associated with each information. The intermediate layer calculates an output value from each information input via the input layer using various functions, thresholds, and the like, and outputs the calculated output value to the output layer. The learning model 12M includes a treatment time output layer and a fee output layer as output layers, outputs information related to the treatment time via the treatment time output layer, and outputs information related to the fee via the fee output layer. The treatment time output layer includes a plurality of output nodes respectively associated with preset treatment times, and each output node outputs a probability that a treatment time needs to be discriminated (or identified) as the treatment time associated with each output node. In the example illustrated in FIG. 3, each output node is associated with each time zone (i.e., treatment times) such as less than 0.5 hours, 0.5 hours or more and less than 1 hour, 1 hour or more and less than 1.5 hours, and the like. The time zone associated with each output node is not limited to the examples as set forth above. The output value of each output node from the treatment time output layer can be, for example, a value of 0 to 1, and a sum of the probabilities output from the respective output nodes is 1.0 (100%). Furthermore, the fee output layer includes a plurality of output nodes respectively associated with preset fees (treatment fees), and each output node outputs a probability that a fee needs to be discriminated as the fee associated with each output node. In the example illustrated in FIG. 3, each output node is associated with each price range, for example, of less than 100,000 yen, 100,000 yen or more and less than 250,000 yen, 250,000 yen or more and less than 500,000 yen, and the like. The price range associated with each output node is not limited to the examples as set forth above. The output value of each output node from the fee output layer can be, for example, a value of 0 to 1, and a sum of the probabilities output from the respective output nodes is 1.0 (100%). According to the above-described configuration, the learning model 12M according to the present embodiment outputs information related to the treatment time and the fee required for the catheter treatment scheduled to be performed on the patient when receiving an input of the patient information and the treatment information of the patient.

The information processing device 10 specifies as a treatment time that needs to be predicted a treatment time associated with the output node that has output a maximum output value (discrimination probability) among the output values from the treatment time output layer in the above-described learning model 12M, and specifies as the fee that needs to be predicted the fee associated with the output node that has output the maximum output value (discrimination probability) among the output values from the fee output layer. The treatment time output layer of the learning model 12M may employ a configuration including one output node that outputs a treatment time having a highest discrimination probability instead of including the plurality of output nodes that output the discrimination probabilities for respective treatment times. Furthermore, the fee output layer of the learning model 12M may employ a configuration including one output node that outputs a fee having the highest discrimination probability instead of including a plurality of output nodes that output the discrimination probabilities for respective fees.

The learning model 12M learns about a patient for whom catheter treatment has been performed, using training data obtained by giving information (correct answer label) indicating a treatment time and a fee actually required for the executed catheter treatment to patient information of the patient and the executed treatment information. The patient information, the executed treatment information, and the actual treatment time and fee can be obtained from the patient information and the treatment information of the treated patient registered in the medical DB 12*a*. In a case where the actual treatment time and fee are not registered in the medical DB 12*a*, the actual treatment time and fee can be calculated from the treatment information of the treated patient registered in the medical DB 12*a*. When receiving an input of the patient information and the treatment information included in the training data, the learning model 12M performs learning such that an output value from the output node associated with the correct answer label (treatment time and fee) included in the training data becomes close to 1, and the output value from another output node becomes close to 0. More specifically, the learning model 12M performs an arithmetic operation in the intermediate layer based on the input patient information and treatment information, and calculates an output value from each output node of the treatment time output layer. Furthermore, the learning model 12M compares the calculated output value of each output node, and a value (0 or 1) associated with the correct answer label, and optimizes a parameter such as a weight between neurons in the intermediate layer and the treatment time output layer such that each output value approximates a value associated with each correct answer label. The learning model 12M optimizes data such as coefficients and thresholds of various functions used for an arithmetic operation in the intermediate layer and the treatment time output layer using, for example, a backpropagation method. Similarly, the learning model 12M performs an arithmetic operation in the intermediate layer based on the input patient information and treatment information, and calculates an output value from each output node of the fee output layer. Furthermore, the learning model 12M compares the calculated output value of each output node, and a value (0 or 1) associated with the correct answer label, and optimizes a parameter such as a weight between neurons in the intermediate layer and the fee output layer using, for example, a backpropagation method such that each output value approximates a value associated with each correct answer label. Consequently, it is possible to obtain the learning model 12M that has learned to output the treatment time and the fee required for the catheter treatment related to the treatment information when receiving an input of the patient information and the treatment information.

The learning of the learning model 12M may be performed by another learning device. The learned learning model 12M generated by causing another learning device to perform learning is downloaded from the learning device to the information processing device 10 via, for example, the network or the portable storage medium 1*a*, and stored in the storage unit 12. The learning model 12M is not limited to the configuration illustrated in FIG. 3. The learning model 12M can be configured to receive an input of various pieces of information that influence the treatment time and the fee required for catheter treatment.

Figure 4:
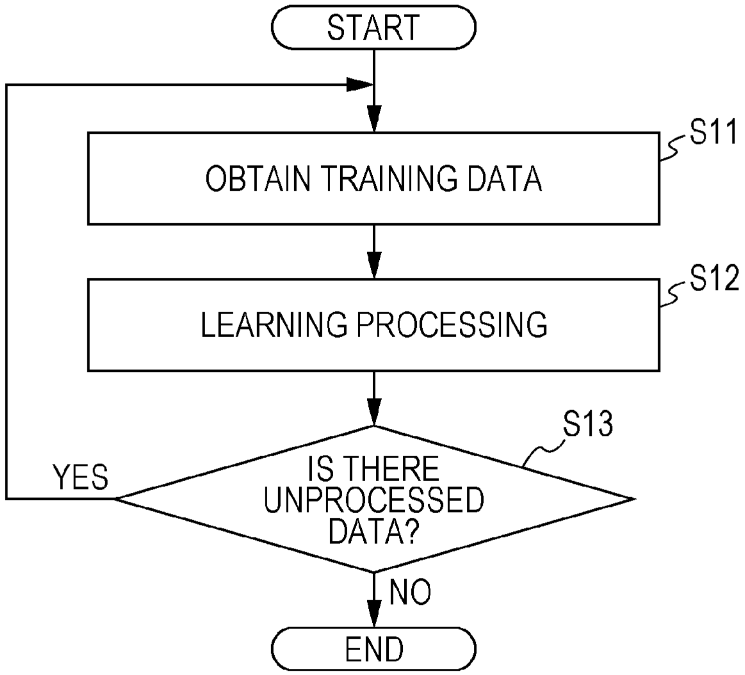
FIG. 4 is a flowchart illustrating an example of a processing procedure of generating the learning model.

Hereinafter, processing of learning training data and generating the learning model 12M will be described. FIG. 4 is a flowchart illustrating an example of a processing procedure of generating the learning model 12M. The following processing is performed by the control unit 11 of the information processing device 10 according to the control program 12P stored in the storage unit 12, yet may be performed by another learning device.

The control unit 11 of the information processing device 10 obtains the training data obtained by giving a correct treatment time and fee to the patient information and the treatment information (S11). The patient information and the treatment information for the training data are patient information of a patient for whom catheter treatment has been performed and information related to treatment contents of the catheter treatment performed on the patient, and the patient information and the treatment information stored in the medical DB 12*a* can be used therefor. As the correct treatment time and fee, the treatment information (an actual treatment time and fee) of the treated patient stored in the medical DB 12*a* can be used. In a case where the actual treatment time and fee are not stored in the medical DB 12*a*, if a start date and time and an end date and time of the catheter treatment are stored in the treatment information of the medical DB 12*a*, it is possible to calculate the treatment time based on the start date and time and the end date and time, and, if insurance points of a medical insurance required for the catheter treatment are stored in the treatment information of the medical DB 12*a*, it is possible to calculate the fee (treatment fee) based on the insurance points. The training data may be generated in advance from the stored contents of the medical DB12*a*, and registered in a training data DB. In the case of the training data being registered or stored in a training data DB, the control unit 11 may obtain the training data from the training data DB.

The control unit 11 performs learning processing of the learning model 12M using the obtained training data (S12). Here, the control unit 11 inputs the patient information and the treatment information included in the training data to the learning model 12M, and obtains the treatment time and the fee as outputs. The control unit 11 compares the output treatment time and fee with the correct treatment time and fee, and optimizes parameters such as weights between neurons in the intermediate layer and the output layer (the treatment time output layer and the fee output layer) using, for example, the backpropagation method such that both of the output treatment time and fee and the correct treatment time and fee approximate. More specifically, the control unit 11 causes the learning model 12M to perform learning such that an output value from an output node associated with the correct treatment time and fee becomes close to 1, and an output value from another output node becomes close to 0.

The control unit 11 decides whether or not there is unprocessed data (S13). For example, the control unit 11 decides whether or not there is information that is not yet processed by learning processing among the patient information and the treatment information of the patient for whom catheter treatment has been performed. Furthermore, in a case where the training data is registered in the training data DB in advance, the control unit 11 decides whether or not there is unprocessed training data among the training data stored in the training data DB. When it is decided that there is the unprocessed data (S13: YES), the control unit 11 returns to the processing in S11, performs the processing in S11 and S12 based on the information of the patient that is not yet processed by the learning processing, and repeats the learning processing using the training data. When deciding that there is no unprocessed data (S13: NO), the control unit 11 finishes a series of processing.

The above-described processing generates the learning model 12M that has learned to output the treatment time and the fee required for the catheter treatment related to the treatment information when receiving an input of the patient information and the treatment information of the patient. Note that it is possible to further optimize the learning model 12M by repeatedly performing the above-described learning processing using the training data. Furthermore, it is possible to cause the already learned learning model 12M to perform relearning by performing the above-described processing, and in this case, it is possible to generate the learning model 12M with higher differentiation accuracy. For example, by causing the learning model 12M to learn training data per medical institution, it is possible to generate the learning model 12M matching each medical institution. Treatment times and fees of catheter treatment differ depending on a facility in a catheter treatment room, a technique of the person in charge (surgeon), or the like, and therefore by generating the learning model 12M per medical institution, it is possible to predict a treatment time and a fee that take the facility of each medical institution and the technique of the person in charge into account.

Figure 5:
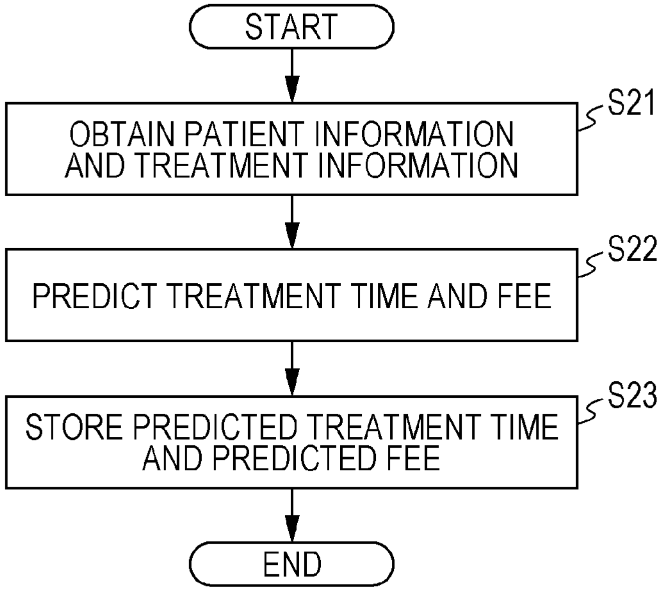
FIG. 5 is a flowchart illustrating an example of a processing procedure of predicting a treatment time and a fee.

Processing of predicting a treatment time and a fee required for catheter treatment scheduled to be performed, using the learning model 12M generated by the above-described processing will be described below. FIG. 5 is a flowchart illustrating an example of a processing procedure of predicting a treatment time and a fee. The following processing is performed by the control unit 11 of the information processing device 10 according to the control program 12P stored in the storage unit 12.

In a case where a treatment time and a fee of catheter treatment are predicted for a patient scheduled to be subjected to the catheter treatment, the control unit 11 (obtaining unit) of the information processing device 10 obtains patient information and treatment information of the patient from the medical DB 12*a* (S21). The control unit 11 inputs the obtained patient information and treatment information to the learning model 12M, and predicts the treatment time and fee based on an output value from the learning model 12M (S22). For example, the control unit 11 specifies an output node that has output a maximum output value (discrimination probability) among the output nodes from the treatment time output layer in the learning model 12M, and specifies the treatment time (time zone) associated with the specified output node as the treatment time required for the catheter treatment scheduled to be performed. Furthermore, the control unit 11 specifies an output node that has output the maximum output value (discrimination probability) among the output nodes from the fee output layer, and specifies the fee (price range) associated with the specified output node as the fee required for the catheter treatment scheduled to be performed.

The control unit 11 stores the respectively predicted treatment time and fee in the medical DB 12*a* (S23). More specifically, the control unit 11 stores the respectively predicted treatment time and fee as a predicted treatment time and a predicted fee associated with a patient ID of the patient scheduled to be subjected to the catheter treatment in the medical DB 12*a*. The control unit 11 (output unit) may generate a display screen (display information) that displays the predicted treatment time and fee in association with the patient information and the treatment information of the patient, cause the display unit 15 or another display device to display the display screen, and present the display screen to the user.

According to the above-described processing, by using the learning model 12M that has learned the training data, the information processing device 10 according to the present embodiment can predict the treatment time and the fee required for the catheter treatment scheduled to be performed on the patient from the patient information and the treatment information of the patient. Particularly in a case where the learning model 12M is caused to learn a large amount of training data, it is possible to realize the learning model 12M that can predict a more accurate treatment time and fee. Consequently, it is possible to present for the catheter treatment that is not yet performed the treatment time and the fee based on the patient information and the treatment information of the patient. Furthermore, in the present embodiment, the fee required for the catheter treatment is predicted using the learning model 12M, so that it is possible to predict the fee based on the insurance points (medical fee points) of the medical insurance. Furthermore, by predicting the fee (insurance points) of the catheter treatment in this way, it is possible to use the predicted fee (insurance points) when creating an insurance application form (medical reward statement) after the treatment, and it is possible to automatically create the insurance application form.

The above-described present embodiment has employed the configuration where information of a person in charge of catheter treatment is included in treatment information and input to the learning model 12M. In addition, for example, the learning model 12M may be generated per person in charge of catheter treatment in each medical institution. In this case, the learning model 12M is caused to learn about each person in charge by using training data obtained by giving information (correct answer label) indicating an actually required treatment time and fee to patient information of a patient for whom catheter treatment has been performed by the person in charge, and executed treatment information. In this case, too, as the patient information, the executed treatment information, and the actual treatment time and fee, the patient information and the treatment information of the treated patient registered in the medical DB 12*a* can be used. In a case of such a configuration, the learning model 12M is configured to not receive an input of information of a person in charge of catheter treatment. Furthermore, the learning model 12M configured to not receive an input of the information of the person in charge of catheter treatment may weigh a treatment time and a fee predicted based on an output value from the learning model 12M according to the person in charge of the catheter treatment to use as a predicted treatment time and a predicted fee. In this case, it is possible to predict the treatment time and the fee that take the technique, an experience value, and the like of each person in charge into account per person in charge. Furthermore, for each of the plurality of medical institutions, the learning model 12M may be generated per medical institution.

The present embodiment employs a configuration where the information processing device 10 locally performs processing of predicting a treatment time and a fee using the learning model 12M, yet is not limited to this configuration. For example, the information processing device 10 may be configured as a server computer, and the server computer may be configured to perform the processing of predicting the treatment time and the fee using the learning model 12M. In this case, the server computer may be configured to output the predicted treatment time and fee to, for example, a display device connected via a network to display. Furthermore, there may be employed a configuration where a first server that performs processing of predicting the treatment time and the fee using the learning model 12M, and a second server that performs storage processing of the medical DB 12*a* (electronic clinical record) are separately provided. In this case, the first server can be configured to obtain patient information and treatment information of a patient from the second server, and perform the processing of predicting the treatment time and fee using the learning model 12M. Even in a case where such a configuration is employed, it is possible to perform processing similar to that of the present embodiment, and obtain a similar effect.

Embodiment 2

An information processing device will be described that performs processing of predicting a treatment time and a fee required for catheter treatment scheduled to be performed from patient information and treatment information of a patient based on a rule. More specifically, an information processing device will be described that searches for a similar case similar to the patient information and the treatment information of the patient scheduled to be subjected to the catheter treatment from a database that stores patient information and treatment information (past cases) of patients for whom the catheter treatment has been performed, and predicts the treatment time and the fee required for the catheter treatment scheduled to be performed based on the searched similar case. The information processing device according to the present embodiment employs the same configuration as that of an information processing device 10 according to embodiment 1, and therefore detailed description of the configuration will be omitted. Note that the information processing device 10 according to the present embodiment stores a case DB 12*b* instead of a learning model 12M in a storage unit 12. The case DB 12*b* may be stored in another storage device connected to the information processing device 10, or may be stored in another storage device with which the information processing device 10 can communicate.

FIG. 6 is a schematic view illustrating a configuration example of the case DB 12*b*. The case DB 12*b* is a database that stores case data related to catheter treatment performed in the past. The case DB 12*b* illustrated in FIG. 6 includes a case identifier (ID) column, a patient information column, a treatment information column, and the like. The case ID column stores identification information (case IDs) for identifying each case. Each of the patient information column and the treatment information column stores patient information and treatment information of a patient of catheter treatment performed in the past in association with the case ID. As the patient information and the treatment information, information similar to the patient information and the treatment information stored in a medical DB 12*a* illustrated in FIG. 2 can be used. A treatment time and a fee of the treatment information stored in the case DB 12*b* are an actual treatment time and fee. The case ID to be stored in the case DB 12*b* is issued and stored by a control unit 11 every time new case information is registered. Other information stored in the case DB 12*b* is stored by the control unit 11 when the control unit 11 obtains the other information via an input unit 14 or a communication unit 13. Storage contents of the case DB 12*b* is not limited to the example illustrated in FIG. 6, and various pieces of information related to a patient, and various pieces of information related to the treatment performed on the patient may be stored.

The information processing device 10 according to the present embodiment predicts the treatment time and the fee required for the catheter treatment according to the patient information and the treatment information based on the case DB 12*b*. More specifically, the information processing device 10 specifies information similar to the patient information and the treatment information of the patient scheduled to be subjected to catheter treatment from patient information and treatment information of each case registered in the case DB 12*b*. Furthermore, the information processing device 10 specifies (predicts) a treatment time and a fee of the specified treatment information as the treatment time and the fee of the catheter treatment scheduled to be performed. For example, the case DB 12*b* may be prepared per person in charge of catheter treatment in a medical institution, or may be prepared for each of a plurality of medical institutions.

Figure 7:
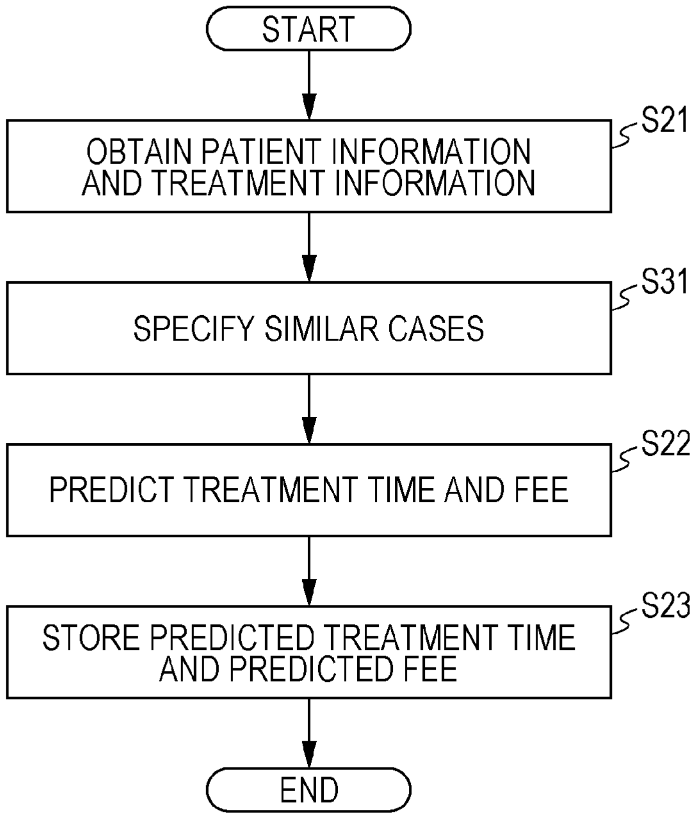
FIG. 7 is a flowchart illustrating an example of a processing procedure of predicting a treatment time and a fee according to embodiment 2.

Processing of predicting a treatment time and a fee required for catheter treatment scheduled to be performed using the case DB 12*b* will be described below. FIG. 7 is a flowchart illustrating an example of a processing procedure of predicting a treatment time and a fee according to embodiment 2. The processing illustrated in FIG. 7 is processing where S31 is added between S21 and S22 in the processing illustrated in FIG. 5. Description of the same processes or steps as those in FIG. 5 will be omitted.

The control unit 11 of the information processing device 10 according to the present embodiment performs the same processing as that of S21 illustrated in FIG. 5. That is, the control unit 11 obtains patient information and treatment information of a patient scheduled to be subjected to catheter treatment from the medical DB 12*a*. Next, the control unit 11 specifies a similar case similar to the patient information and the treatment information of the patient scheduled to be subjected to catheter treatment among the cases stored in the case DB 12*b* (S31). For example, the control unit 11 compares each information of patient information and treatment information, and each information of the patient information and the treatment information of the patient scheduled to be treated, and calculates a similarity score for each case stored in the case DB 12*b*. In a case where, for example, each information of the patient information and the treatment information is the same, the similarity score may be obtained by adding a score matching each information (each item), and using a total value of the scores as the similarity score. Furthermore, the control unit 11 may compare each information of patient information and treatment information of each case, and each information of the patient information and the treatment information of the patient scheduled to be treated, calculate similarity of each information, add a score of each information (each item) according to the similarity, and use the total value of the scores as the similarity score.

When calculating the similarity, the control unit 11 extracts a feature amount from each comparison target information, and calculates the similarity of each feature amount. When, for example, each information is text data, a feature amount extraction method can be performed using, for example, a feature extractor configured as an RNN or Doc2vec. Such a feature extractor accepts an input of text data of patient information and treatment information, and outputs a vector representing a feature amount of the text data. Furthermore, in a case where each information is image information (medical image), a feature amount can be extracted using, for example, the feature extractor configured as a CNN. Such a feature extractor accepts an input of a medical image included in patient information, and outputs a feature amount (feature map) of the medical image (image data). The CNN includes an intermediate layer (hidden layer) in which convolution layers for convoluting input data and pooling layers in which the convoluted data is mapped are alternately connected, and extracts a feature amount of the input data (generates a feature map) in the intermediate layer. Subsequently, the control unit 11 calculates similarity of the feature amount extracted from each information. Although a method for calculating the similarity is not particularly limited, the control unit 11 calculates, for example, cosine similarity of a feature amount represented by a vector. By calculating the similarity of each information (each item), and adding a score corresponding to the similarity, the control unit 11 calculate for each case a similarity score with respect to a patient scheduled to be subjected to catheter treatment. The control unit 11 specifies for each case stored in the case DB 12*b* a case having the highest similarity score calculated as described above as a similar case.

Furthermore, the control unit 11 reads the treatment time and the fee of the specified similar case from the case DB 12*b*, and specifies (predicts) the treatment time and the fee required for the catheter treatment scheduled to be performed (S22). The control unit 11 stores the predicted treatment time and fee as a predicted treatment time and a predicted fee associated with a patient ID of the patient scheduled to be subjected to the catheter treatment in the medical DB 12*a* (S23). The control unit 11 may generate a display screen (display information) that displays the predicted treatment time and fee in association with the patient information and the treatment information of the patient, and cause a display unit 15 or another display device to display the display screen. In the present embodiment, according to the above-described processing, it is possible to predict the treatment time and the fee required for the catheter treatment scheduled to be performed, based on the case data similar to the catheter treatment scheduled to be performed among case data of catheter treatment performed in the past. Consequently, in the present embodiment, too, it is possible to present for the catheter treatment that is not yet performed the treatment time and the fee based on the patient information and the treatment information of the patient.

In the present embodiment, it is possible to obtain the same effect as that of above-described embodiment 1. Furthermore, in the present embodiment, when a great number of items of case data are collected, it is possible to obtain case data that is more similar to the catheter treatment scheduled to be performed, and it is possible to predict a more accurate treatment time and fee based on the more similar case data. The modified example described as appropriate in above-described embodiment 1 is applicable to the present embodiment, too. For example, the information processing device 10 may be configured such that a server computer performs processing of predicting a treatment time and a fee based on the case DB 12*b*. In this case, the server computer may be configured to output the predicted treatment time and fee to, for example, a display device connected via a network to display. Even in a case where such a configuration is employed, it is possible to perform processing similar to that of the present embodiment, and obtain a similar effect.

Furthermore, in the present embodiment, the treatment time and the fee in a case (similar case) having a maximum similarity score with the catheter treatment scheduled to be performed among the cases stored in the case DB 12*b* are the treatment time and the fee for the catheter treatment scheduled to be performed. In addition, a plurality of cases having high similarity scores with respect to the catheter treatment scheduled to be performed may be specified, and the treatment time and the fee of the catheter treatment scheduled to be performed may be calculated from the treatment times and the fees of the plurality of specified cases.

Embodiment 3

An information processing device will be described that predicts for catheter treatment scheduled to be performed, a treatment time (working time) and a fee required for each of a plurality of procedures of the catheter treatment. The information processing device according to the present embodiment employs the same configuration as that of an information processing device 10 according to embodiment 1, and therefore detailed description of the configuration will be omitted. In the information processing device 10 according to the present embodiment, a learning model stored in a storage unit 12 is slightly different from a learning model 12M according to embodiment 1 illustrated in FIG. 3. Furthermore, the information processing device 10 according to the present embodiment stores a treatment time and a fee in association with each of a plurality of procedures of catheter treatment in a treatment information field in a medical DB 12*a* stored in the storage unit 12. Here, too, the treatment time and the fee are a treatment time and a fee predicted from patient information and treatment information, or an actual treatment time and fee.

Figure 8:
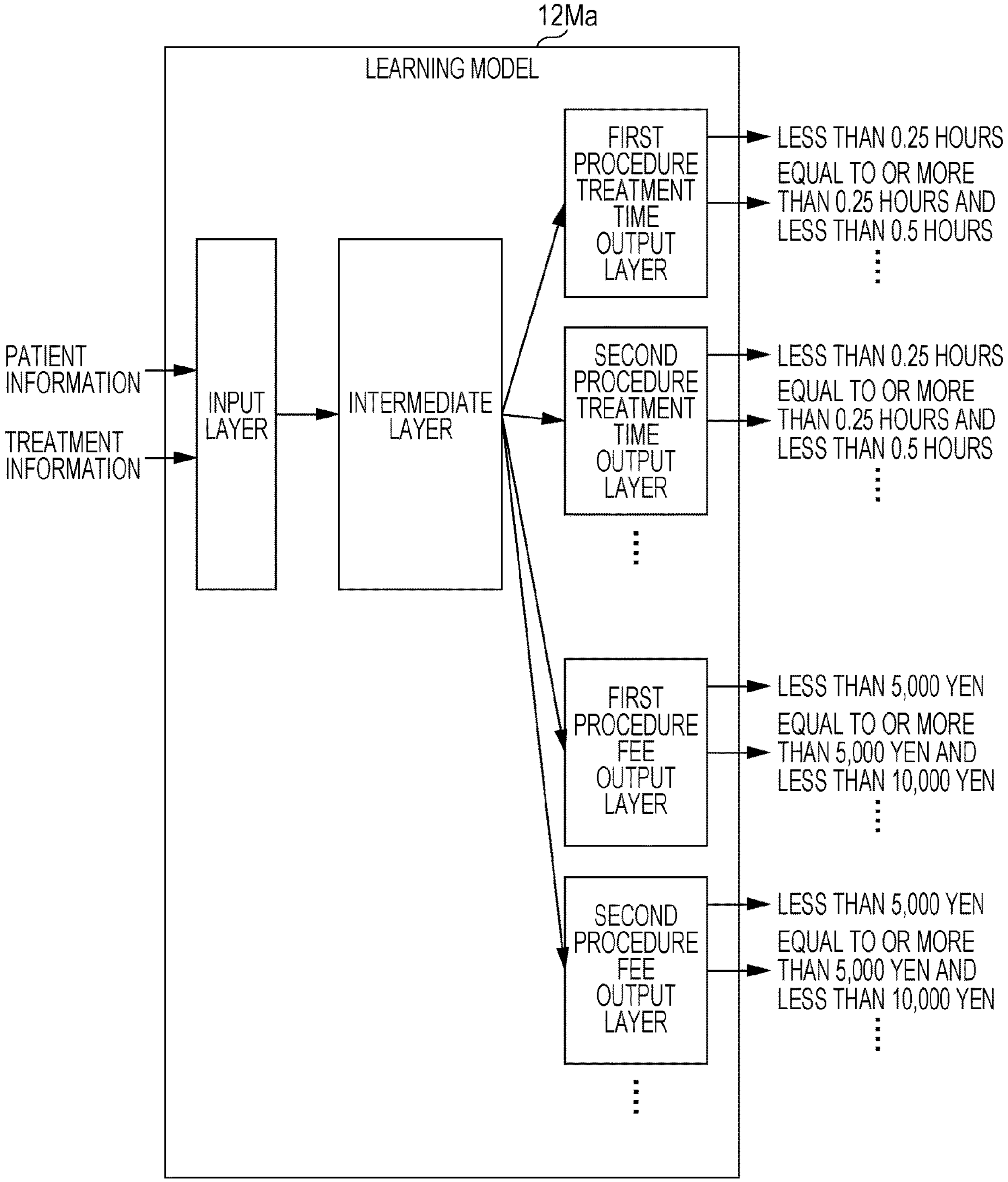
FIG. 8 is a schematic view illustrating a configuration example of a learning model according to embodiment 3.

FIG. 8 is a schematic view illustrating a configuration example of the learning model according to embodiment 3. A learning model 12Ma according to the present embodiment is a machine learning model that receives an input of the patient information and the treatment information, and outputs the treatment time and the fee required for each of a plurality of procedures of the catheter treatment related to the treatment information. The learning model 12Ma may be configured using an algorithm such as a CNN, an RNN, an LSTM, a GAN, a decision tree, a random forest, or an SVM, or may be configured by combining a plurality of algorithms. The information processing device 10 according to the present embodiment inputs patient information and treatment information of a patient registered in the medical DB 12*a* to the learning model 12Ma, and predicts a treatment time and a fee of each procedure of the catheter treatment based on an output value from the learning model 12Ma.

The learning model 12Ma illustrated in FIG. 8 includes an input layer to which patient information and treatment information are input, output layers that output treatment times (working times) and fees of each procedure of catheter treatment, and an intermediate layer that extracts a feature amount from the input information. The input layer and the intermediate layer are similar to those of the learning model 12M of embodiment 1 illustrated in FIG. 3. The learning model 12Ma according to the present embodiment includes, as the output layers, a plurality of treatment time output layers that output information related to the treatment time of each procedure of a first procedure, a second procedure and nth procedures (i.e., a plurality of procedures) of catheter treatment, and a plurality of fee output layers that output information related to a fee of each procedure. Each treatment time output layer includes a plurality of output nodes respectively associated with preset time zones (treatment times), and each output node outputs a discrimination probability for a time zone (treatment time) associated with each output node. Furthermore, each fee output layer includes a plurality of output nodes respectively associated with preset price ranges, and each output node outputs a discrimination probability for a price range associated with each output node. The time zone associated with each output node of each treatment time output layer and the price range associated with each output node of each fee output layer are not limited to the example illustrated in FIG. 8, and may be a different time zone (treatment time) and price range depending on each procedure. The learning model 12Ma employing the above-described configuration outputs information related to the treatment time and the fee required for each procedure of the catheter treatment scheduled to be performed on the patient when receiving an input of the patient information and the treatment information of the patient.

The information processing device 10 specifies as a treatment time that needs to be predicted for a corresponding procedure a treatment time associated with the output node that has output a maximum output value among the output values from the respective treatment time output layers in the above-described learning model 12Ma, and specifies as the fee that needs to be predicted for the corresponding procedure the fee associated with the output node that has output the maximum output value among the output values from the respective fee output layers. Note that each treatment time output layer of the learning model 12Ma may employ a configuration including one output node that outputs a treatment time having a highest discrimination probability instead of including a plurality of output nodes that output discrimination probabilities for the respective treatment times. Furthermore, each fee output layer of the learning model 12Ma may employ a configuration including one output node that outputs a fee having a highest discrimination probability instead of including a plurality of output nodes that output discrimination probabilities for the respective fees.

The learning model 12Ma learns about a patient for whom catheter treatment has been performed, using training data obtained by giving information (correct answer label) indicating a treatment time and a fee of each procedure actually required for the executed catheter treatment to patient information and the executed treatment information of the patient. When receiving an input of the patient information and the treatment information included in the training data, the learning model 12Ma performs an arithmetic operation in the intermediate layer based on the input patient information and treatment information, and calculates an output value from each output node. For each of the treatment time output layers and the fee output layers, the learning model 12Ma compares the output value from each output node and a value (0 or 1) associated with a correct answer label, and optimizes a parameter such as a weight between neurons in the intermediate layer and the output layer (the treatment time output layer and the fee output layer) using, for example, a backpropagation method such that each output value approximates a value associated with each correct answer label. Consequently, it is possible to obtain the learning model 12Ma that has learned to output the treatment time and the fee required for each procedure of the catheter treatment when receiving an input of the patient information and the treatment information.

In the information processing device 10 according to the present embodiment, a control unit 11 generates the learning model 12Ma illustrated in FIG. 8 by executing processing similar to the processing illustrated in FIG. 4. In the information processing device 10 according to the present embodiment, the learning model 12Ma performs learning using training data obtained by giving a correct treatment time and fee of each procedure of catheter treatment to patient information and treatment information.

Figure 9:
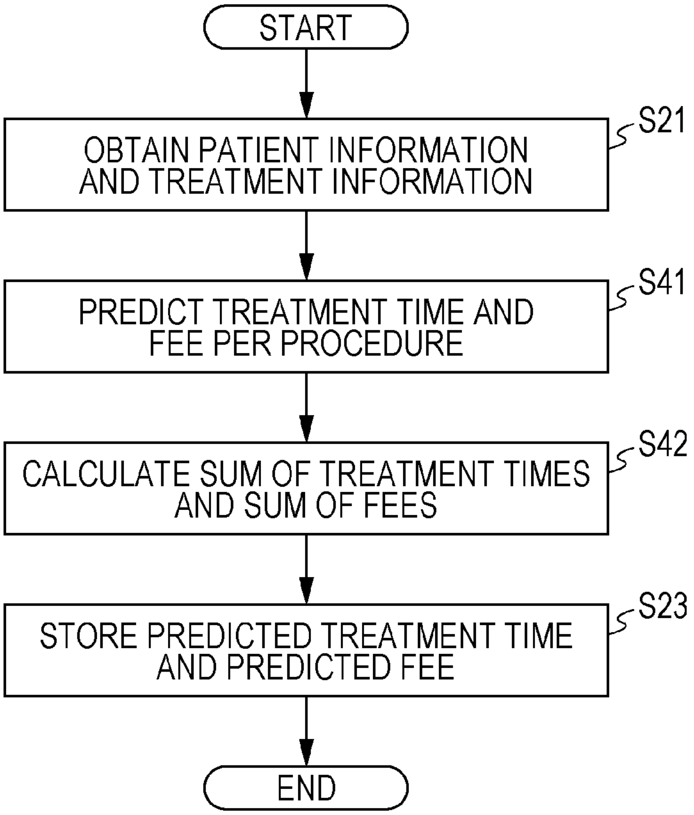
FIG. 9 is a flowchart illustrating an example of a processing procedure of predicting a treatment time and a fee according to embodiment 3.

Processing of predicting a treatment time and a fee required for each procedure of catheter treatment scheduled to be performed using the learning model 12Ma will be described below. FIG. 9 is a flowchart illustrating an example of a processing procedure of predicting a treatment time and a fee according to embodiment 3. The processing illustrated in FIG. 9 is processing where S41 and S42 are added instead of S22 in the processing illustrated in FIG. 5. Description of the same as those in FIG. 5 will be omitted.

The control unit 11 of the information processing device 10 according to the present embodiment performs the same processing as that of S21 illustrated in FIG. 5. That is, the control unit 11 obtains patient information and treatment information of a patient scheduled to be subjected to catheter treatment from the medical DB 12*a*. Next, the control unit 11 inputs the obtained patient information and treatment information to the learning model 12Ma, and predicts a treatment time and a fee of each procedure of the catheter treatment based on an output value from the learning model 12Ma (S41). For example, the control unit 11 specifies an output node that has output a maximum output value among the output nodes of the first procedure treatment time output layer in the learning model 12Ma, and specifies the treatment time (time zone) associated with the specified output node as the treatment time required for the first procedure of the catheter treatment scheduled to be performed. Furthermore, the control unit 11 specifies an output node that has output the maximum output value among the output nodes from the first procedure fee output layer, and specifies the fee (price range) associated with the specified output node as the fee required for the first procedure of the catheter treatment scheduled to be performed. The control unit 11 predicts treatment times and fees of all procedures by similar processing.

The control unit 11 calculates a sum of the predicted treatment times of the respective procedures and a sum of the predicted fees of the respective procedures (S42). Consequently, the control unit 11 can predict the treatment time and the fee of the catheter treatment scheduled to be performed. Furthermore, the control unit 11 stores the predicted treatment time and fee in association with a patient ID of the patient scheduled to be subjected to the catheter treatment in the medical DB 12*a* (S23). In the present embodiment, the control unit 11 may store the treatment time and the fee predicted for each procedure in association with each procedure of the catheter treatment in the medical DB 12*a*. The control unit 11 may generate a display screen that displays the predicted treatment time and fee in association with the patient information and the treatment information of the patient, and cause a display unit 15 or another display device to display the display screen. At this time, the control unit 11 may cause the display unit 15 or the other display device to display a display screen that displays the treatment time and the fee predicted for each procedure of the catheter treatment in association with the patient information and the treatment information of the patient.

In the present embodiment, it is possible to obtain the same effect as that of each of the above-described embodiments. Furthermore, in the present embodiment, the treatment time and the fee are predicted for each of a plurality of procedures of catheter treatment, so that it is possible to more accurately predict the treatment time and the fee. Furthermore, in the present embodiment, it is possible to present a treatment time and a fee predicted per procedure for catheter treatment that is not yet performed, and it is possible to present a breakdown of each procedure of the treatment time and the fee required for the catheter treatment. Furthermore, the modified example described as appropriate in each of above-described embodiments is applicable to the present embodiment, too. Furthermore, similar to embodiment 2, the present embodiment may also employ a configuration where processing of predicting a treatment time and a fee required for each procedure of catheter treatment scheduled to be performed is performed based on a rule. Even in a case where such a configuration is employed, it is possible to perform processing similar to that of the present embodiment, and obtain a similar effect.

Embodiment 4

An information processing device will be described that reserves (allocates) a catheter treatment room (i.e., a treatment room) by using a predicted treatment time required for catheter treatment scheduled to be performed based on patient information and treatment information of a patient. The information processing device according to the present embodiment employs the same configuration as that of an information processing device 10 according to embodiment 1, and therefore detailed description of the configuration will be omitted. Furthermore, in the information processing device 10 according to the present embodiment, a control unit 11 generates a learning model 12M illustrated in FIG. 3 by executing processing similar to the processing illustrated in FIG. 4, and stores the learning model 12M in a storage unit 12.

Figure 10:
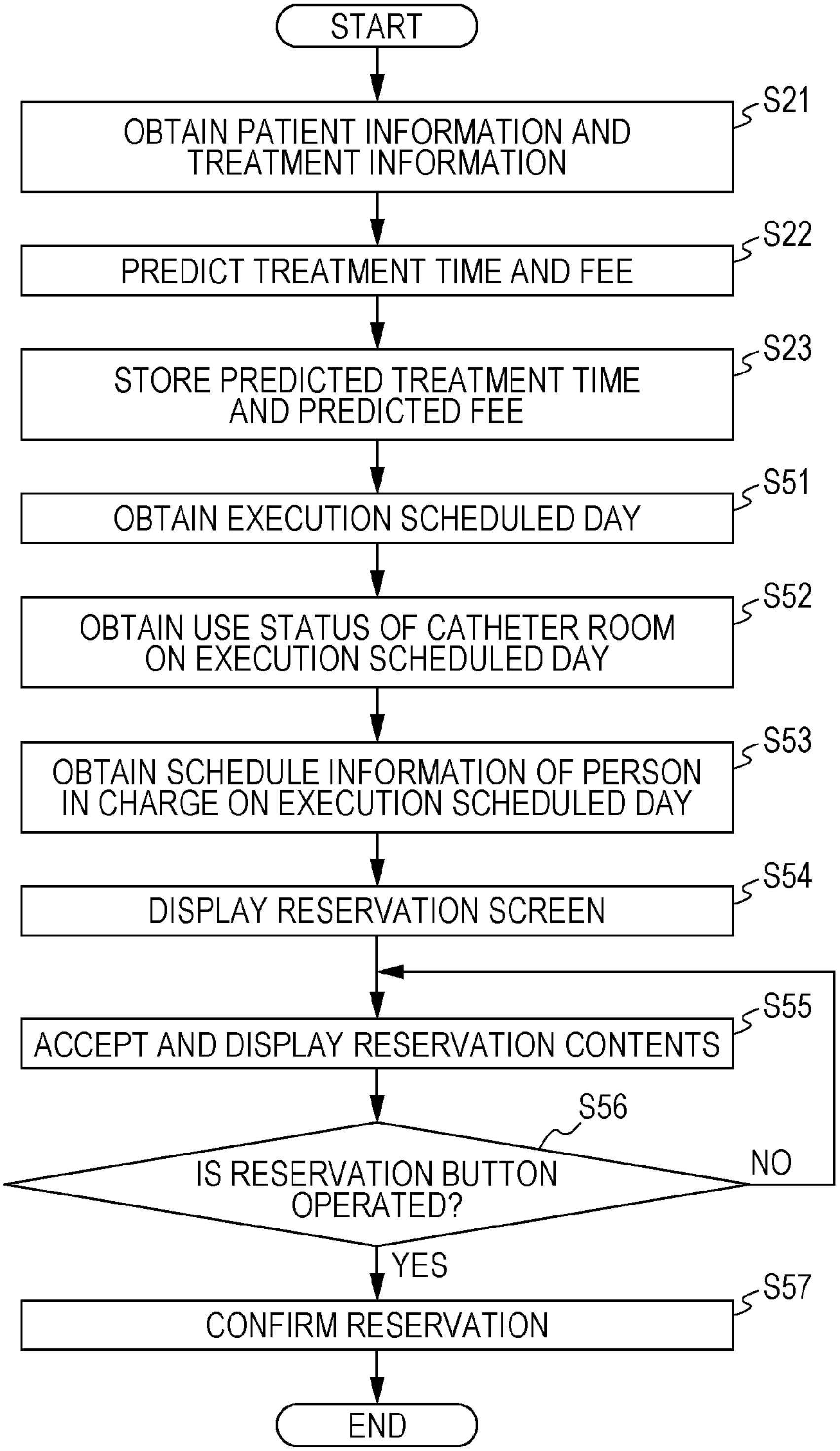
FIG. 10 is a flowchart illustrating an example of a processing procedure of predicting a treatment time and a fee according to embodiment 4.
Figure 11:
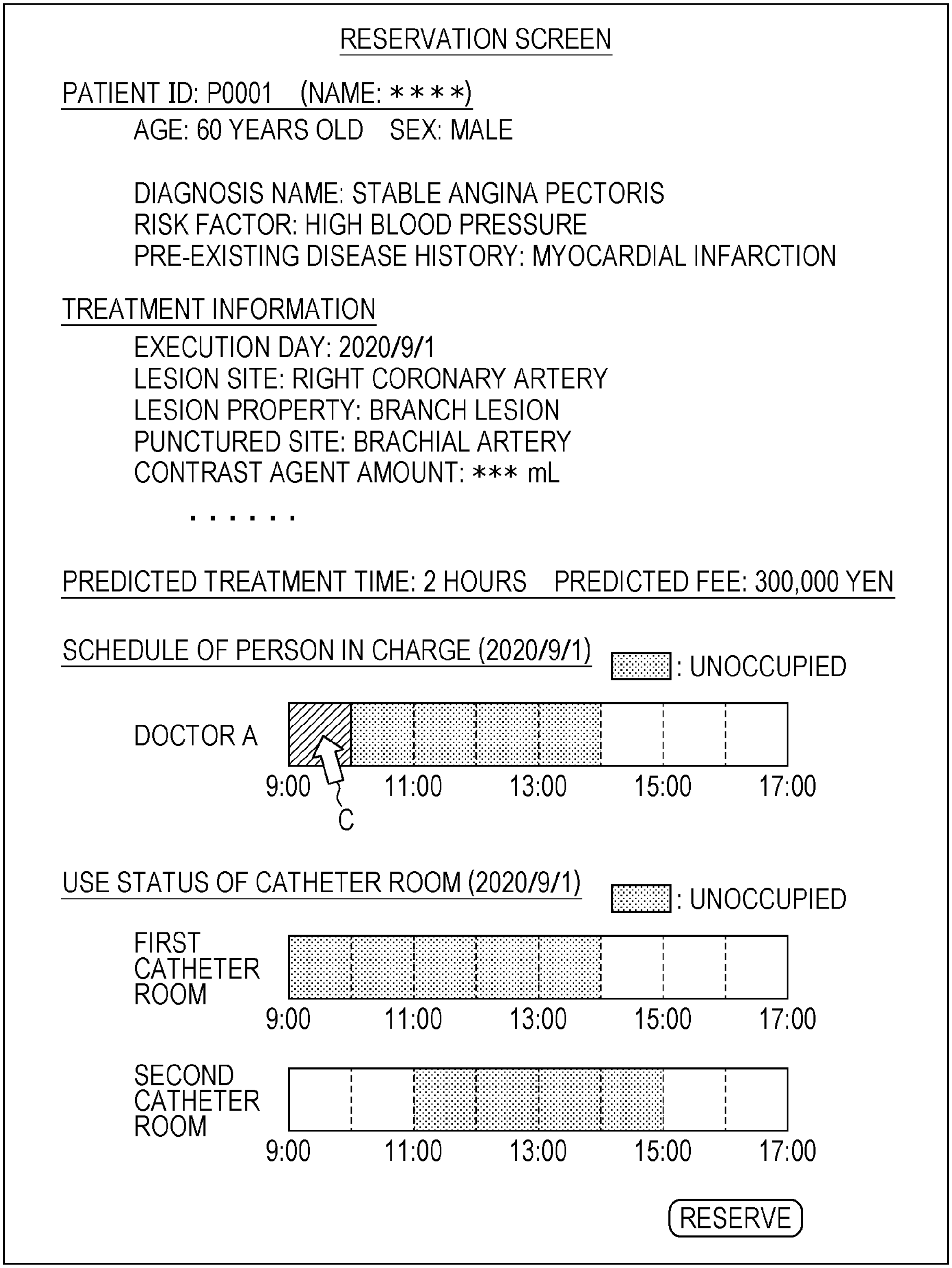
FIG. 11 is a schematic view illustrating a screen example.

FIG. 10 is a flowchart illustrating an example of a processing procedure of predicting a treatment time and a fee according to embodiment 4, and FIG. 11 is a schematic view illustrating a screen example. The processing illustrated in FIG. 10 is processing where S51 to S57 are added after S23 in the processing illustrated in FIG. 5. Description of the same processes or steps as those in FIG. 5 will be omitted.

The control unit 11 of the information processing device 10 according to the present embodiment performs the same processing as those of S21 to S23 illustrated in FIG. 5. Consequently, a treatment time and a fee for a catheter treatment scheduled to be performed are stored in a medical DB 12*a*. Next, the control unit 11 obtains an execution scheduled day of catheter treatment for a patient for whom a treatment time and a fee have been predicted (S51). The execution scheduled day of the catheter treatment can be, for example, a date desired by a person in charge (medical worker) or the patient, and the control unit 11 obtains the execution scheduled day designated via, for example, the input unit 14, or reads the execution scheduled day from the medical DB 12*a* in a case where the designated execution scheduled day is stored in the medical DB 12*a*.

Next, the control unit 11 obtains a use status of the catheter treatment room (referred to as catheter room below) on the execution scheduled day (S52), and obtains schedule information (schedule) of the person in charge on the execution scheduled day (S53). The use status of the catheter room is stored in the storage unit 12 or another storage device in association with dates and times (a use start date and time and a use end date and time) and a patient ID of a treatment target patient, and the control unit 11 obtains the use status of the catheter room on the execution scheduled day from the storage unit 12 or the other storage device. Note that, in a case where there are a plurality of catheter rooms, the control unit 11 obtains a use status of each catheter room. Furthermore, a schedule of the person in charge is also stored in the storage unit 12 or the other storage device, and the control unit 11 obtains the schedule of the person in charge on the execution scheduled day from the storage unit 12 or the other storage device.

The control unit 11 generates a reservation screen displaying the use status of the catheter room on the execution scheduled day and the schedule of the person in charge to display on the display unit 15 (S54). FIG. 11 illustrates a reservation screen example, and the reservation screen illustrated in FIG. 11 displays patient information and treatment information of a treatment target patient, a predicted treatment time and fee, a schedule of a person in charge on an execution scheduled day, and the use status of the catheter room. The schedule of the person in charge is displayed so as to make it possible to distinguish a time zone (unoccupied time zone, i.e., a time of day) in which catheter treatment can be performed, and a time zone (i.e., another time of day) in which catheter treatment cannot be performed within working hours of the person in charge. Note that already registered work contents may be displayed in a time zone in which catheter treatment cannot be performed in the schedule of the person in charge. The use status of the catheter room is displayed so as to make it possible to distinguish a time zone (unoccupied time zone) in which the catheter room can be used, and a time zone in which the catheter room cannot be used within a time in which the catheter room can be used. Note that a patient ID and treatment contents of the patient for whom the reservation has already been made may be displayed in a time zone in which the catheter room cannot be used in the use status of the catheter room. The reservation screen is configured such that display fields of the schedule of the person in charge and the use status of the catheter room respectively accept reservations for persons in charge and catheter rooms. By performing, for example, a drag and drop operation on the schedule of the person in charge via an input unit 14 as indicated by, for example, a cursor C in FIG. 11, it is possible to make a reservation for the person in charge. FIG. 11 illustrates a state where a reservation for a doctor A at 9:00 to 10:00 is designated. Similarly, by performing a drag and drop operation on the use status of the catheter room on the reservation screen, it is possible to make a reservation for the catheter room.

The control unit 11 accepts a reservation for the person in charge and the catheter room via the input unit 14 to display the accepted reservation contents (S55). More specifically, when accepting the reservation for the person in charge and the catheter room, the control unit 11 indicates the accepted time zone in a mode indicating the reservation. For example, in the example illustrated in FIG. 11, the accepted time zone (i.e., time slot) is indicated by a hatching different from hatchings indicating unoccupied time zones. Furthermore, the reservation screen includes a reservation button for instructing confirmation of the accepted reservation for the person in charge and the catheter room. Therefore, the control unit 11 decides whether or not the reservation button of the reservation screen has been operated (S56), and, when deciding that the reservation button has been operated (S56: YES), confirms the reservation with the accepted reservation contents (S57). More specifically, the control unit 11 stores a catheter treatment execution schedule in the reserved time zone in the schedule of the person in charge stored in the storage unit 12 or the other storage device, and stores a catheter room use schedule in the reserved time zone in the use status of the catheter room.

When it is decided that the reservation button is not operated (S56: NO), the control unit 11 returns to the processing in S55, and continues accepting reservations via the reservation screen until the reservation button is operated. In the present embodiment, according to the above-described processing, after predicting the treatment time and the fee required for the catheter treatment scheduled to be performed, it is possible to make a reservation for the person in charge and the catheter room based on the predicted treatment time. There may be employed a configuration where, instead of accepting a reservation for a person in charge and a catheter room via the reservation screen in the above-described processing, the reservation is automatically made in an unoccupied time zone of the person in charge and the catheter room based on the predicted treatment time.

In the present embodiment, it is possible to obtain the same effect as that of each of the above-described embodiments. Furthermore, in the present embodiment, it is possible to make a reservation for a person in charge and a catheter room based on a treatment time predicted for catheter treatment scheduled to be performed, and it is possible to manage the use status of the catheter room and the schedule of the person in charge. By accurately predicting the treatment time required for the catheter treatment, it is possible to efficiently make a reservation for the person in charge and the catheter room. Consequently, it is possible to improve a use rate of the catheter room, and reduce waiting times of persons in charge and achieve optimal human resource allocation. As a result, contribution to making management of each medical institution efficient is expected. Furthermore, the configuration of the present embodiment is applicable to the information processing device 10 according to embodiments 2 and 3, too, and a similar effect can be obtained even in a case where the configuration is applied to the information processing device 10 according to embodiments 2 and 3. Furthermore, the modified example described as appropriate in each of above-described embodiments is applicable to the present embodiment, too.

Embodiment 5

An information processing device employing a configuration of an information processing device 10 according to embodiment 4 where a person in charge (medical worker) is not taken into account when predicting a treatment time and a fee required for catheter treatment scheduled to be performed will be described. The information processing device according to the present embodiment is configured to present a selectable person in charge and catheter room based on a predicted treatment time, and accept a reservation for the presented person in charge and catheter room. The information processing device according to the present embodiment employs the same configuration as that of the information processing device 10 according to embodiment 1, and therefore detailed description of the configuration will be omitted. In the information processing device 10 according to the present embodiment, a control unit 11 generates a learning model 12M illustrated in FIG. 3 by executing processing similar to the processing illustrated in FIG. 4, and stores the learning model 12M in a storage unit 12. Note that the learning model 12M according to the present embodiment is configured to not include information of a person in charge in treatment information to be input. That is, the learning model 12M of the present embodiment receives an input of patient information of a patient and treatment information that does not include information of a person in charge, and outputs a treatment time and a fee required for catheter treatment related to the treatment information.

Figure 12:
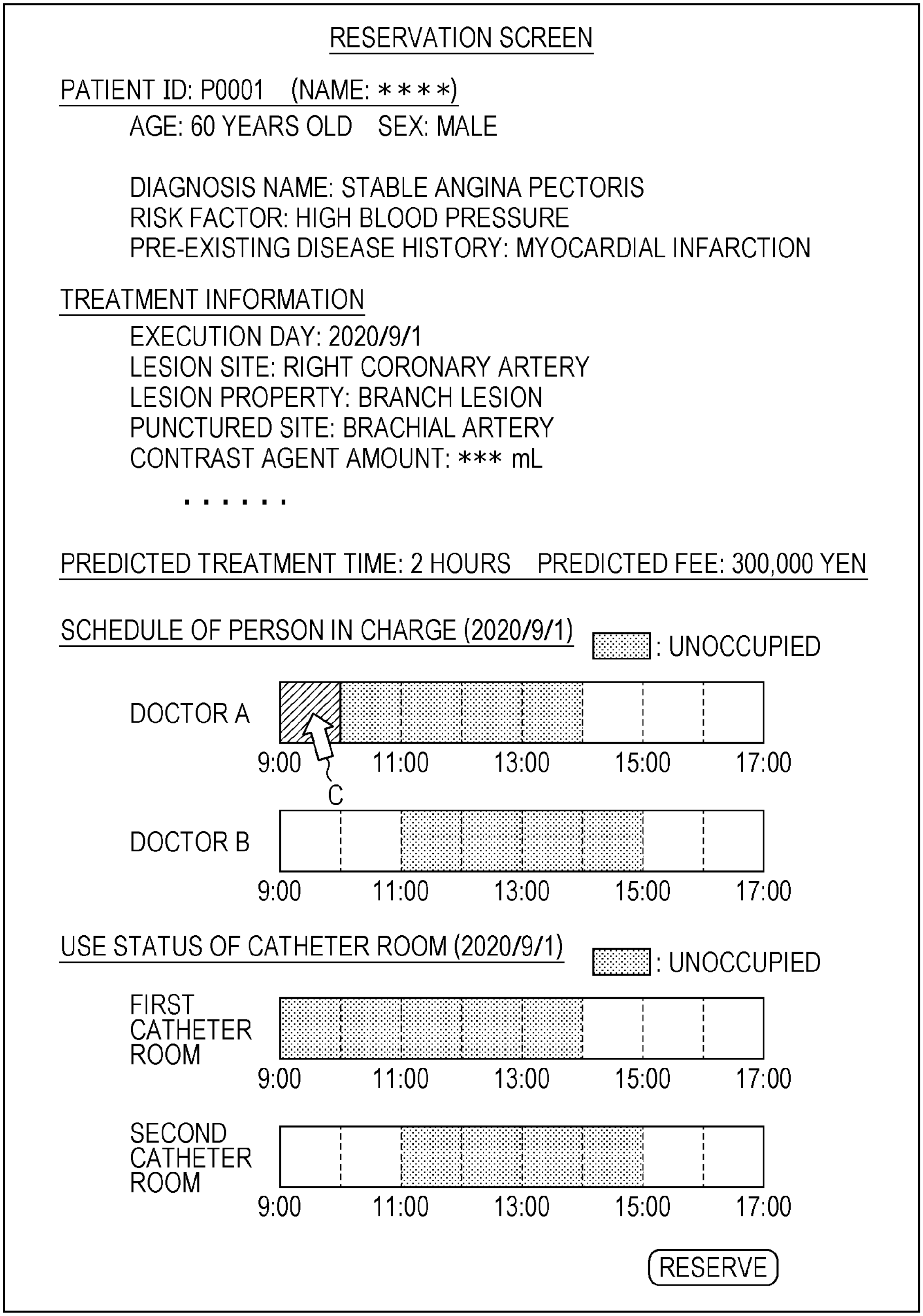
FIG. 12 is a schematic view illustrating a reservation screen example according to embodiment 5.

FIG. 12 is a schematic view illustrating a reservation screen example according to embodiment 5. In the information processing device 10 according to the present embodiment, the control unit 11 executes processing similar to the processing illustrated in FIG. 10. In the present embodiment, in S53, the control unit 11 obtains schedule information (schedule) of an execution scheduled day for all persons in charge (medical workers) who can perform catheter treatment. The control unit 11 may extract persons in charge who can secure a predicted treatment time from all the persons in charge, and obtain the schedule information of the execution scheduled day for the extracted person in charge. Furthermore, the control unit 11 causes a display unit 15 to display a reservation screen as illustrated in FIG. 12 (S54), and presents a use status of a catheter room and the schedule of the person in charge on the execution scheduled day of the catheter treatment. The reservation screen illustrated in FIG. 12 employs the same configuration as that of the reservation screen illustrated in FIG. 11, yet displays schedules of a plurality of persons in charge on an execution scheduled day.

The control unit 11 accepts a reservation for one of persons in charge and one of catheter rooms also on the reservation screen illustrated in FIG. 12 via display fields of the schedules of the persons in charge and the use status of the catheter rooms. Therefore, the control unit 11 displays accepted reservation contents when accepting the reservation for one of the persons in charge and one of the catheter rooms via the reservation screen (S55), and confirms the reservation with the accepted reservation contents (S57) when deciding that a reservation button on the reservation screen has been operated (S56: YES). In the present embodiment, according to the above-described processing, it is possible to present a person in charge and a catheter room that can be reserved based on a predicted treatment time after predicting a treatment time and a fee required for catheter treatment scheduled to be performed, and make a reservation for a person in charge and a catheter room according to presented contents.

In the present embodiment, it is possible to obtain the same effect as that of each of the above-described embodiments. Furthermore, in the present embodiment, it is possible to present a person in charge and a catheter room that can be reserved based on a treatment time predicted for the catheter treatment scheduled to be performed, and select and reserve an arbitrary person in charge and catheter room. The modified example described as appropriate in each of the above-described embodiments is applicable to the present embodiment, too.

Embodiment 6

An information processing device will be described that predicts a treatment time (working time) and a fee required for each remaining procedure (work) in an information processing device 10 according to embodiment 3 by taking into account technique information (execution treatment information) related to work (technique) that has been performed and is being performed while catheter treatment is performed. The information processing device according to the present embodiment employs the same configuration as that of an information processing device 10 according to embodiment 1, and therefore detailed description of the configuration will be omitted. The information processing device 10 according to the present embodiment stores in the storage unit 12 a learning model 12Ma according to embodiment 3 illustrated in FIG. 8, and, in addition, an in-treatment learning model 12Mb that predicts a treatment time and a fee required for each remaining procedure based on technique information while the catheter treatment is performed.

Figure 13:
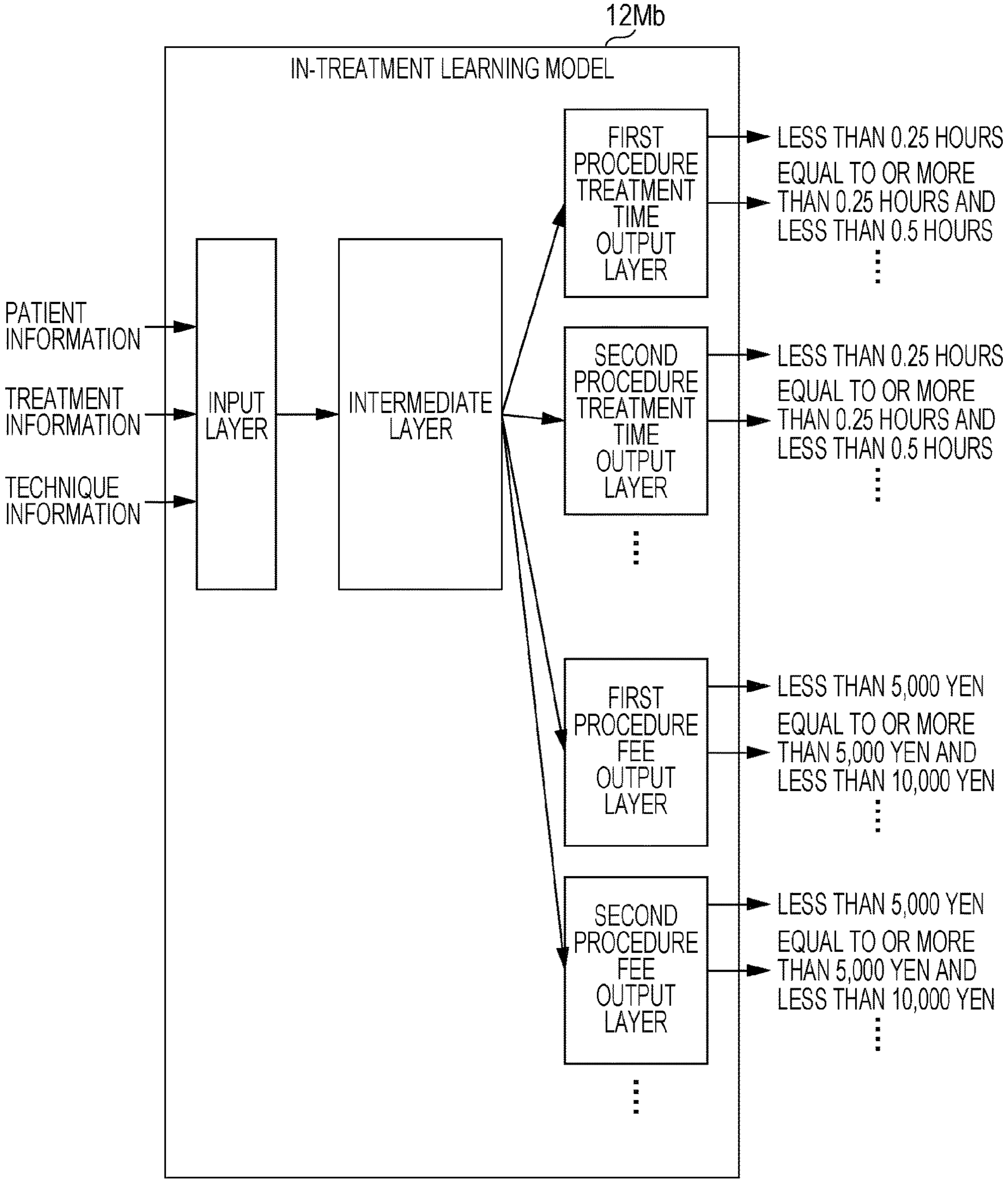
FIG. 13 is a schematic view illustrating a configuration example of an in-treatment learning model.

FIG. 13 is a schematic view illustrating a configuration example of the in-treatment learning model 12Mb. The in-treatment learning model 12Mb can be a machine learning model that receives an input of technique information in addition to patient information and treatment information, and outputs a treatment time and a fee required for each procedure of a plurality of procedures of catheter treatment. The in-treatment learning model 12Mb may be configured using an algorithm such as an RNN, an LSTM, a CNN, a GAN, a decision tree, a random forest, or an SVM, or may be configured by combining a plurality of algorithms. The information processing device 10 according to the present embodiment inputs patient information and treatment information of a patient registered in a medical DB 12*a*, and technique information input during catheter treatment to the in-treatment learning model 12Mb, and predicts a treatment time and a fee of each remaining procedure based on an output value from the in-treatment learning model 12Mb. The technique information can include, for example, information of pharmaceutical agents and medical equipment used in each procedure of catheter treatment, a treatment time (required time) actually required for each performed procedure, an elapsed time from start of the catheter treatment, and the like.

The in-treatment learning model 12Mb illustrated in FIG. 13 employs the same configuration as that of the learning model 12Ma illustrated in FIG. 8 except that the in-treatment learning model 12Mb receives an input of technique information in addition to patient information and treatment information via an input layer. The in-treatment learning model 12Mb employing the above-described configuration outputs information related to a treatment time and a fee required for each procedure of catheter treatment that is being performed when receiving an input of the patient information and the treatment information of a patient, and the technique information. Also in the in-treatment learning model 12Mb, each treatment time output layer may employ a configuration including one output node that outputs a treatment time having a highest discrimination probability instead of including a plurality of output nodes that output the discrimination probabilities for respective treatment times, and each fee output layer may employ a configuration including one output node that outputs a fee having the highest discrimination probability instead of including a plurality of output nodes that output discrimination probabilities for respective fees.

The in-treatment learning model 12Mb learns about a patient for whom catheter treatment has been performed, using training data obtained by giving information (correct answer label) indicating a treatment time and a fee required for each actually performed procedure to patient information of the patient, the executed treatment information, and the technique information of each executed procedure. When receiving an input of the patient information, the treatment information, and the technique information included in the training data, the in-treatment learning model 12Mb performs an arithmetic operation in an intermediate layer based on the input information, and calculates an output value from each output node. The in-treatment learning model 12Mb compares the output value from each output node and a value (0 or 1) associated with a correct answer label for each of the treatment time output layers and the fee output layers, and optimizes a parameter such as a weight between neurons in the intermediate layer and the output layer using, for example, a backpropagation method such that each output value approximates a value associated with each correct answer label. Consequently, it is possible to obtain the in-treatment learning model 12Mb that has learned to output the treatment time and the fee required for each procedure of the catheter treatment when receiving an input of the patient information, the treatment information, and the technique information.

In the information processing device 10 according to the present embodiment, a control unit 11 generates the learning model 12Ma illustrated in FIG. 8 and the in-treatment learning model 12Mb by executing processing similar to the processing illustrated in FIG. 4. The information processing device 10 according to the present embodiment predicts for the catheter treatment that is not yet performed the treatment time and the fee of each procedure using the learning model 12Ma, and predicts for the catheter treatment that is being performed the treatment time and the fee of each procedure using the in-treatment learning model 12Mb after the catheter treatment is performed.

Figure 14:
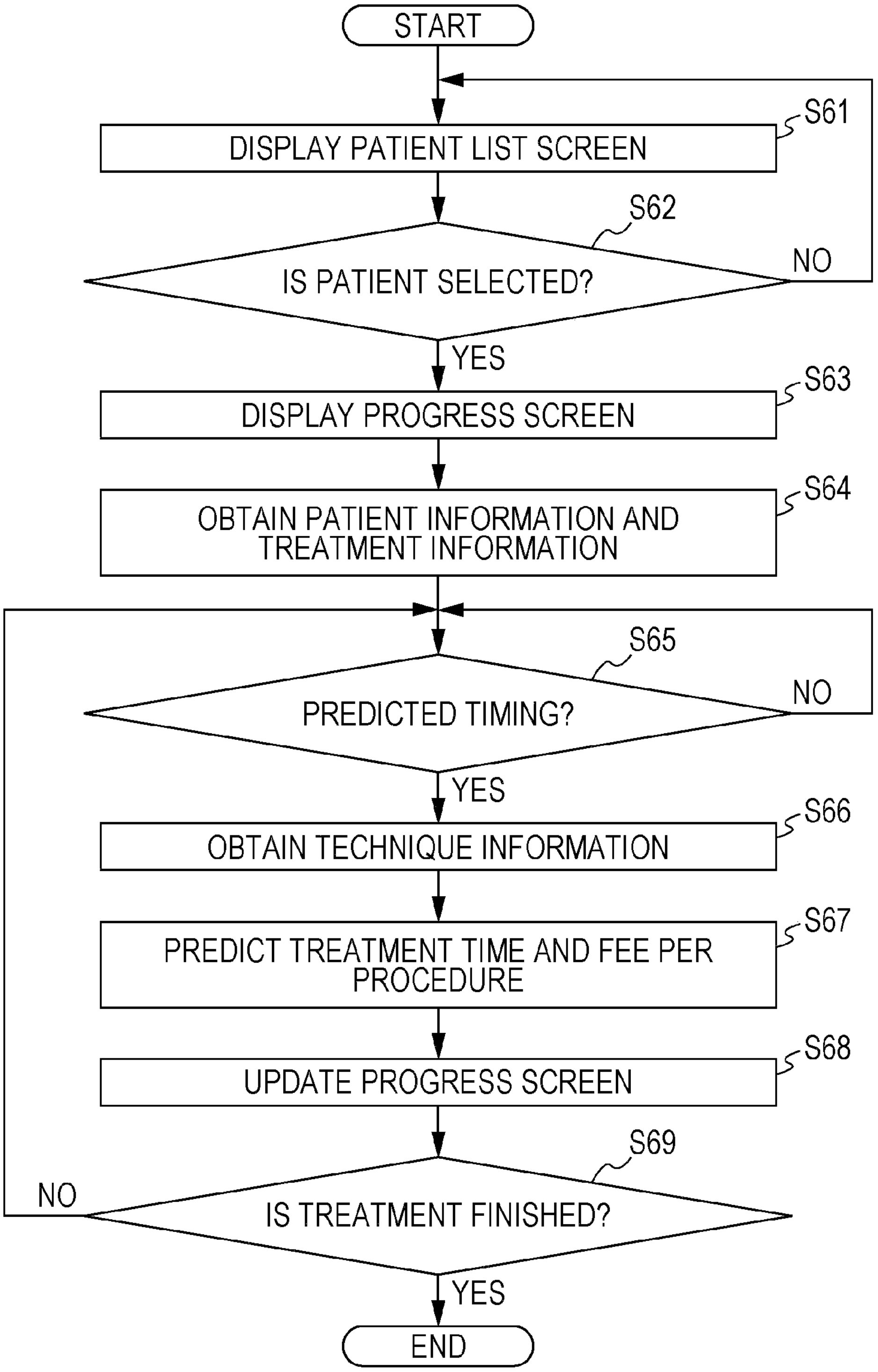
FIG. 14 is a flowchart illustrating an example of a processing procedure of predicting a treatment time and a fee.

Processing of predicting a treatment time and a fee required for each procedure using the in-treatment learning model 12Mb while catheter treatment is performed will be described below. FIG. 14 is a flowchart illustrating an example of a processing procedure of predicting a treatment time and a fee, and FIGS. 15A and 15B are schematic views illustrating screen examples. The following processing is performed by the control unit 11 of the information processing device 10 according to the control program 12P stored in the storage unit 12.

By executing processing similar to the processing illustrated in FIG. 5, the control unit 11 of the information processing device 10 according to the present embodiment predicts the treatment time and the fee required for each procedure of catheter treatment for a patient scheduled to be subjected to catheter treatment. Furthermore, the control unit 11 performs following processing when the catheter treatment is performed. When the catheter treatment is performed, the control unit 11 causes a display unit 15 to displays a patient list screen illustrated in FIG. 15A (S61). The patient list screen displays information related to each patient scheduled to be subjected to catheter treatment today. The patient list screen displays, for each patient, an execution scheduled date and time of catheter treatment (a date, a start time, and an end time), information of a catheter room to be used, patient information (a patient ID, a name, an age, a sex, a diagnosis name), treatment information (treatment contents and a person in charge), and the like. The start time and the end time of the catheter treatment are displayed with parentheses ("(" and ")") when each time does not pass. The example illustrated in FIG. 15A indicates that, while a start time of catheter treatment of a patient whose patient ID is P0011 has passed, an end time has not passed, and indicates that the catheter treatment of this patient is being performed (a technique is being performed).

The patient list screen is configured to accept selection of one of the displayed patients, and the control unit 11 decides whether one of the patients has been selected via an input unit 14 (S62). When it is decided that no patient is selected (S62: NO), the control unit 11 returns to the processing in S61, and continues displaying the patient list screen. When it is decided that one of the patients has been selected (S62: YES), the control unit 11 causes the display unit 15 to display a progress screen of the selected patient (S63). As illustrated in FIG. 15B, the progress screen displays for the selected patient a start time (time), treatment contents (progress), a required time, a pharmaceutical agent and medical equipment necessary for the treatment, a fee (insurance points), and the like per procedure of the catheter treatment. The required time of each procedure is a treatment time of each procedure predicted by using the learning model 12Ma, and the time of each procedure is a time calculated by adding the required time of each procedure to the start time (scheduled start time) of the catheter treatment. The time of each procedure is displayed with parentheses ("(" and ")") when each procedure is not yet performed. The example illustrated in FIG. 15B illustrates that a procedure after POBA (Plain Old Balloon Angioplasty), i.e., dilation treatment of a lesion using a balloon, has not yet been performed, and right Coronary Angiography (right CAG) treatment is currently being performed (the technique is being performed).

The field of the pharmaceutical agent/medical equipment on the progress screen is configured to accept an input via the input unit 14, and a medical staff inputs information of the pharmaceutical agent and medical equipment used for each treatment during catheter treatment. The fields of the time and the required time on the progress screen are also configured to be able to be changed via the input unit 14, and the medical staff can change the time and the treatment time to the time at which each procedure is actually started and the treatment time (required time) actually required for each procedure during catheter treatment. Input of various pieces of information described herein may be voice input via a microphone in addition to input from a keyboard, or may be input performed by reading a code such as a barcode or a QR Code® given to each pharmaceutical agent and medical equipment.

The control unit 11 displays, for example, a progress screen, and obtains patient information and treatment information of a treatment target patient from the medical DB 12*a* after preparation to perform catheter treatment is completed (S64). Furthermore, the control unit 11 decides whether or not a timing to execute processing of predicting the treatment time and the fee of each procedure has come during the catheter treatment (S65). The timing to execute the prediction processing during the catheter treatment may come, for example, every predetermined time or every time each procedure is completed. When the prediction processing is performed every predetermined time, the control unit 11 decides whether or not the execution timing has come according to whether or not a predetermined time has elapsed from latest prediction processing. Furthermore, when the prediction processing is performed every time, each procedure is completed, the control unit 11 decides whether or not the execution timing has come according to whether or not the procedure that is being performed has been completed. The progress screen can be configured such that the medical staff clicks the time of each procedure in the progress screen when, for example, each procedure is started, and thereby inputs that each procedure has been started, and, according to this configuration, the control unit 11 can decide that the last procedure has been completed when the start of each procedure is input.

When deciding that the execution timing of the prediction processing has not come (S65: NO), the control unit 11 stands by while performing other processing. When deciding that the execution timing of the prediction process has come (S65: YES), the control unit 11 obtains technique information (execution treatment information) of each procedure of the catheter treatment that is being performed (S66). For example, the control unit 11 obtains the required time of each procedure and the information of the pharmaceutical agent/medical equipment displayed on the progress screen at this point of time, and an elapsed time from start of treatment as the technique information. Furthermore, the control unit 11 inputs the patient information and the treatment information obtained in S64 and the technique information obtained in S66 to the in-treatment learning model 12Mb, and predicts the treatment time and the fee of each procedure based on the output value from the in-treatment learning model 12Mb (S67). For example, the control unit 11 specifies as the treatment time of each procedure the treatment time associated with the output node that has output a maximum output value among the output nodes from a treatment time output layer of each procedure in the in-treatment learning model 12Mb, and specifies as the fee of each procedure the fee associated with the output node that has output the maximum output value among the output nodes from the fee output layer of each procedure. The control unit 11 only needs to predict only the treatment time and the fee of unperformed procedures.

In a case where the treatment time and the fee predicted for the unperformed procedures are different from the treatment time and fee displayed on the progress screen, the control unit 11 updates display contents of the progress screen to a newly predicted treatment time and fee (S68). More specifically, the control unit 11 updates the display contents by adding the treatment time predicted for each procedure after a procedure that is being performed based on a start time of this procedure, and calculating a start time of each procedure. At this time, the control unit 11 can calculate a remaining treatment time by calculating a sum of the treatment times predicted for respective unperformed procedures, and can calculate a scheduled end time of treatment by adding the remaining treatment time from the current time.

The control unit 11 decides whether or not the last procedure has been completed and the catheter treatment has been finished (S69), returns to the processing in S65 when deciding that the catheter treatment is not finished (S69: NO), and repeats the processing in S65 to S68. Consequently, every time the execution timing of the prediction processing comes, the control unit 11 can predict the treatment time and the fee of each remaining procedure based on the patient information and the treatment information of the patient and the technique information of each procedure of the catheter treatment that is being performed, and present the treatment time and the fee to the person in charge and the medical staff. When deciding that the catheter treatment has been finished (S69: YES), the control unit 11 finishes a series of processing.

In the present embodiment, it is possible to obtain the same effect as that of each of the above-described embodiments. Furthermore, in the present embodiment, it is possible to predict the treatment time and the fee of each procedure while the catheter treatment is performed, so that it is possible to present an execution schedule of each subsequent procedure of the catheter treatment that is being performed, to medical staffs who are performing the treatment. Furthermore, in the present embodiment, the treatment time and the fee of each remaining procedure are sequentially predicted during the catheter treatment, so that it is possible to accurately predict the scheduled end time of the catheter treatment that is being performed. Therefore, it is possible to efficiently prepare catheter treatment scheduled to be performed next. As a result, it is possible to improve a use rate of a catheter room, so that it is possible to reduce a waiting time of the medical staffs including the person in charge, and achieve relatively optimal human resource allocation. Furthermore, a waiting time of the patient can be shortened, so that it is possible to reduce a relative burden on the patient.

The modified example described as appropriate in each of the above-described embodiments is applicable to the present embodiment, too. Furthermore, similar to embodiment 2, the present embodiment may also employ a configuration where processing of predicting a treatment time and a fee required for each procedure of catheter treatment that is being performed is performed based on a rule. That is, instead of the in-treatment learning model 12Mb, a database that associates patient information, treatment information, and technique information of a patient, and an actual treatment time and fee of each procedure may be used to predict the treatment time and the fee required for each procedure of the catheter treatment that is being performed. Even in a case where such a configuration is employed, it is possible to perform processing similar to that of the present embodiment, and obtain a similar effect.

The present embodiment employs the configuration where the treatment time and the fee of each procedure are predicted using the learning model 12Ma according to embodiment 3 illustrated in FIG. 8 before the catheter treatment is performed, yet is not limited to this configuration. There may be employed a configuration where a treatment time and a fee required for catheter treatment scheduled to be performed are predicted using the learning model 12M according to embodiment 1 illustrated in FIG. 3, for example, before the catheter treatment is performed. In this case, too, it is possible to predict the treatment time and the fee of each procedure using the in-treatment learning model 12Mb after the start of the catheter treatment, so that it is possible to predict a remaining treatment time while the catheter treatment is performed, and predict a scheduled end time of the treatment.

Modified Example

Figure 16:
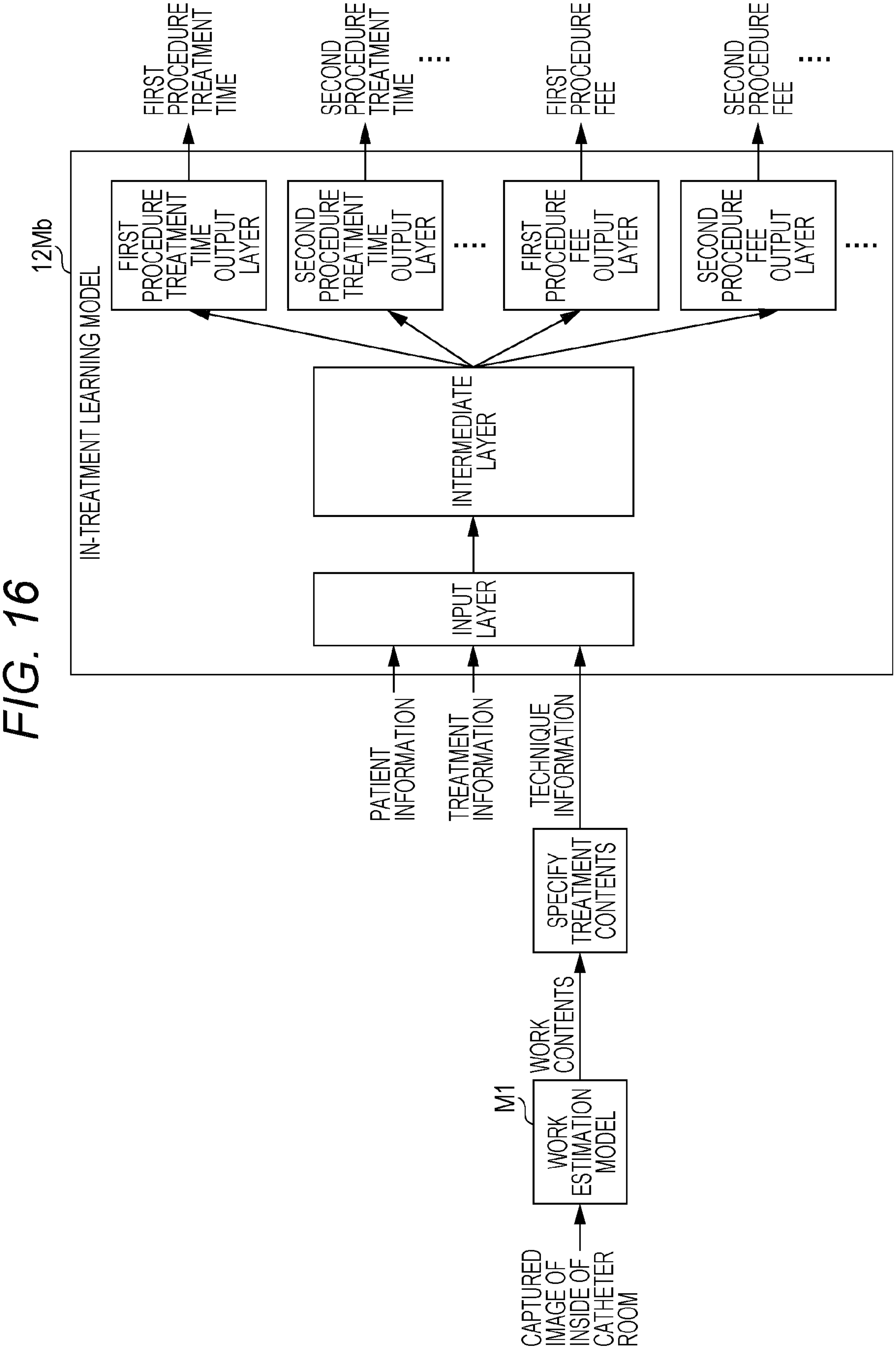
FIG. 16 is an explanatory view related to an in-treatment learning model according to modified example 1.

An aspect will be described where an information processing device 10 according to embodiment 6 analyzes a captured image obtained by capturing an image of an inside of a catheter room, estimates treatment contents from captured actions (work contents) of medical staffs, and information indicating the estimated treatment contents is used as technique information to be input to an in-treatment learning model 12Mb. FIG. 16 is an explanatory view related to the in-treatment learning model 12Mb according to modified example 1. The in-treatment learning model 12Mb according to this modified example employs the same configuration as that of embodiment 6 illustrated in FIG. 13.

In this modified example, the information processing device 10 can include a camera that is installed in a catheter room and captures images of medical staffs who perform catheter treatment, and a work estimation model M1 that estimates work contents performed by the medical staffs in captured images from the captured images captured by the camera. The work estimation model M1 is a machine learning model that receives an input of a captured image of the inside of the catheter room, discriminates work contents (e.g., each procedure of catheter treatment) that is being executed by the captured medical staffs, and outputs a discrimination result. The work estimation model M1 can be configured as, for example, a CNN. For example, the work estimation model M1 includes a plurality of output nodes that are associated with respective procedures of catheter treatment, and each output node outputs a discrimination probability for the procedure associated with each output node. Furthermore, the work estimation model M1 includes a plurality of output nodes that are associated with pharmaceutical agents and medical equipment used in respective procedures of the catheter treatment, and each output node outputs a discrimination probability for the pharmaceutical agent and the medical equipment associated with each output node. Consequently, the information processing device 10 can estimate the work contents of the medical staffs in the captured image, and the pharmaceutical agent and the medical equipment in use based on an output value from the work estimation model M1.

The above-described work estimation model M1 performs learning using training data obtained by giving information (correct answer label) indicating work contents performed by image capturing target medical staffs to the captured image of the inside of the catheter room during catheter treatment performed in the past. The work contents performed by the medical staffs is decided based on each captured image. When receiving an input of the captured image included in the training data, the work estimation model M1 performs learning such that an output value from an output node associated with the correct answer label (work contents) included in the training data becomes close to 1, and an output value from another output node becomes close to 0. More specifically, the work estimation model M1 performs an arithmetic operation in an intermediate layer based on the input captured image, and calculates an output value from each output node. Furthermore, the work estimation model M1 compares the calculated output value of each output node, and a value (0 or 1) associated with the correct answer label, and optimizes a parameter such as a weight between neurons in the intermediate layer and the output layer using, for example, a backpropagation method such that each output value approximates a value associated with each correct answer label.

The control unit 11 of the information processing device 10 according to this modified example inputs to the work estimation model M1 a captured image of an inside of a catheter room captured by the camera while the catheter treatment is performed, and estimates work contents performed by the medical staffs in the captured image based on an output value from the work estimation model M1. The control unit 11 specifies treatment contents (each procedure of the catheter treatment) performed by the medical staffs from the estimated work contents. For example, the control unit 11 specifies treatment (procedure) that is being executed by the medical staffs, a pharmaceutical agent and medical equipment used for each treatment, and a treatment time (required time) required for each treatment. Furthermore, the control unit 11 inputs each specified information as technique information to the in-treatment learning model 12Mb, and thereby predicts the treatment time and the fee of each procedure of the catheter treatment that is being performed.

As described above, in this modified example, the technique information input to the in-treatment learning model 12Mb is estimated by image recognition from a captured image obtained by capturing an image of an execution status of the catheter treatment in the catheter room. That is, in this modified example, in S66 in FIG. 14, the control unit 11 obtains the technique information of each procedure of the catheter treatment that is being performed, by performing image analysis on the captured image of the inside of the catheter room. Note that display contents (information of the pharmaceutical agent and the medical equipment) of a progress screen may be updated based on the technique information obtained from the captured image in this manner.

Also in this modified example, it is possible to predict a treatment time and a fee of each procedure while the catheter treatment is performed, so that it is possible to cause a display unit 15 to display the progress screen illustrated in FIG. 15B during the catheter treatment. Consequently, it is possible to present an execution schedule of each subsequent procedure of the catheter treatment that is being performed, to medical staffs who are performing the treatment.

Embodiment 7

Figure 17:
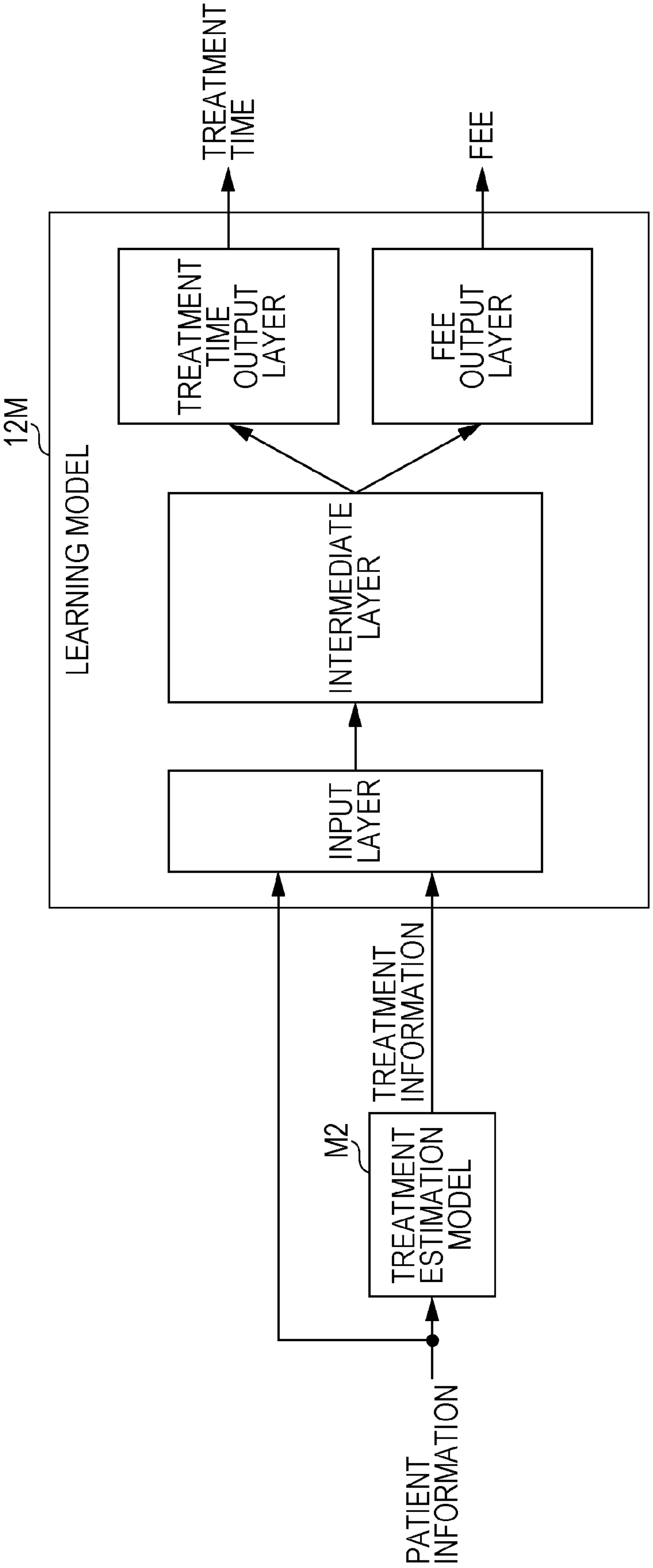
FIG. 17 is an explanatory view related to a learning model according to embodiment 7.

An information processing device will be described that estimates a treatment plan suitable for a patient from patient information, and uses treatment information indicating the estimated treatment plan as an input to a learning model 12M in the information processing device 10 according to embodiment 1. The information processing device according to the present embodiment employs the same configuration as that of an information processing device 10 according to embodiment 1, and therefore detailed description of the configuration will be omitted. FIG. 17 is an explanatory view related to the learning model 12M according to embodiment 7. The learning model 12M according to the present embodiment employs the same configuration as that of embodiment 1 illustrated in FIG. 3.

The information processing device 10 according to the present embodiment includes a treatment estimation model M2 that estimates treatment contents (treatment information) suitable for a patient from patient information. The treatment estimation model M2 is a machine learning model that receives an input of patient information of a treatment target patient, discriminates treatment contents suitable for this patient, and outputs a discrimination result (treatment information). The treatment estimation model M2 can be configured as, for example, a CNN. The patient information includes attribute information of a patient, symptom information, medical records, medical images, and the like, and the treatment information is various pieces of information related to catheter treatment, and includes information related to a lesion, information related to a treatment device, information related to a technique, and the like. For example, the treatment estimation model M2 includes a plurality of output nodes associated with respective discrimination targets per treatment contents that needs to be estimated, and each output node outputs a discrimination probability for the discrimination target associated with each output node. Consequently, the information processing device 10 can specify one discrimination target per treatment contents based on an output value from the treatment estimation model M2, and estimate treatment information of each specified discrimination target.

The information processing device 10 according to the present embodiment estimates the treatment information from the patient information using the treatment estimation model M2, and predicts a treatment time and a fee of the catheter treatment scheduled to be performed from the estimated treatment information and patient information. That is, in the information processing device 10 according to the present embodiment, the control unit 11 obtains only the patient information of the patient from a medical DB 12*a* in S21 in FIG. 5. Subsequently, the control unit 11 inputs the obtained patient information to the treatment estimation model M2, and obtains (estimates) treatment information indicating treatment contents suitable for this patient based on the output value from the treatment estimation model M2. Furthermore, in S22, the control unit 11 inputs the patient information obtained in S21 and the estimated treatment information to the learning model 12M, and predicts the treatment time and the fee based on the output value from the learning model 12M.

In the present embodiment, it is possible to obtain the same effect as that of each of the above-described embodiments. Furthermore, in the present embodiment, the treatment information is estimated from the patient information, so that it is not necessary to input the treatment information via, for example, the input unit 14. Consequently, an operation burden on a person in charge (medical worker) can be reduced. Furthermore, the configuration of the present embodiment is also applicable to the information processing device 10 of embodiments 2 to 6, too, and a similar effect can be obtained even in a case where the configuration is applied to the information processing device 10 according to embodiments 2 to 6. Furthermore, the modified example described as appropriate in each of above-described embodiments is applicable to the present embodiment, too.

The detailed description above describes embodiments of a program, an information processing method, an information processing device, and a model generation method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing a program, which when executed by a computer, performs processing comprising:

obtaining patient information related to a patient for whom catheter treatment is to be performed, and treatment information related to the catheter treatment to be performed on the patient from a database that stores medical data of patients;

predicting a treatment time and fee required for each procedure of the catheter treatment by inputting the patient information and the treatment information into a first learning model;

inputting the predicted treatment time for each procedure of the catheter treatment from the first learning model into a reservation screen for selection of a catheter room among one or more catheter rooms, and wherein the reservation screen displays a use status of one or more catheter rooms indicated by different hatching for accepted time zones and unoccupied times zones;

displaying the predicted treatment time for each procedure on a patient progress screen;

obtaining, while the catheter treatment is performed, execution treatment information related to the catheter treatment that is being performed on the patient, wherein the execution treatment information includes the required time of each completed procedure;

predicting a treatment time and a fee required for unperformed procedures of the catheter treatment by inputting the obtained patient information, the treatment information, and the execution treatment information into a second learning model at a timing when each procedure is completed; and updating the treatment time and the fee required for unperformed procedures of the catheter treatment on the patient progress screen by adding the treatment time predicted for each of the unperformed procedures of the catheter treatment after the timing when each procedure is completed based on a start time of the unperformed procedures of the catheter treatment.

2. The non-transitory computer-readable medium according to claim 1, further comprising:

specifying patient information and treatment information similar to the obtained patient information and treatment information for the unperformed procedures of the catheter treatment from a database that stores a treatment time and a fee required for the catheter treatment in association with the patient information and the treatment information for the unperformed procedures of the catheter treatment; and outputting, by the second learning model, the treatment time and the fee for the unperformed procedures of the catheter treatment associated with the specified patient information and treatment information for the unperformed procedures of the catheter treatment, and a remaining time required until the catheter treatment is finished.

3. The non-transitory computer-readable medium according to claim 1, wherein the patient information includes attribute information of the patient and symptom information indicating a symptom.

4. The non-transitory computer-readable medium according to claim 1, wherein the treatment information includes information related to a physician who performs the catheter treatment, information related to a treatment device used for the catheter treatment, or information related to a technique of the catheter treatment.

5. The non-transitory computer-readable medium according to claim 1, further comprising:

obtaining a captured image of an inside of a catheter room obtained by capturing an execution status of the catheter treatment that is being performed on the patient;

specifying work contents of a physician performing the catheter treatment based on the captured image of the inside of the catheter room; and obtaining the execution treatment information including the required time of each completed procedure based on the specified work contents of the physician performing the catheter treatment based on the captured image of the inside of the catheter room.

6. An information processing device comprising:

a processor configured to:

obtain patient information related to a patient for whom catheter treatment is to be performed, and treatment information related to the catheter treatment to be performed on the patient from a database that stores medical data of patients;

predict a treatment time and fee required for each procedure of the catheter treatment by inputting the patient information and the treatment information into a first learning model;

input the predicted treatment time for each procedure of the catheter treatment from the first learning model into a reservation screen for selection of a catheter room among one or more catheter rooms, and wherein the reservation screen displays a use status of one or more catheter rooms indicated by different hatching for accepted time zones and unoccupied times zones;

display the predicted treatment time for each procedure on a patient progress screen;

obtain, while the catheter treatment is performed, execution treatment information related to the catheter treatment that is being performed on the patient, wherein the execution treatment information includes the required time of each completed procedure;

predict a treatment time and a fee required for unperformed procedures of the catheter treatment by inputting the obtained patient information, the treatment information, and the execution treatment information into a second learning model at a timing when each procedure is completed; and update the treatment time and the fee required for unperformed procedures of the catheter treatment on the patient progress screen by adding the treatment time predicted for each of the unperformed procedures of the catheter treatment after the timing when each procedure is completed based on a start time of the unperformed procedures of the catheter treatment.

7. The information processing device according to claim 6, wherein the processor is configured to:

specify patient information and treatment information similar to the obtained patient information and treatment information for the unperformed procedures of the catheter treatment from a database that stores a treatment time and a fee required for the catheter treatment in association with the patient information and the treatment information for the unperformed procedures of the catheter treatment; and output, by the second learning model, the treatment time and the fee for the unperformed procedures of the catheter treatment associated with the specified patient information and treatment information, and a remaining time required until the catheter treatment is finished.

8. The information processing device according to claim 6, wherein the patient information includes attribute information of the patient and symptom information indicating a symptom.

9. The information processing device according to claim 6, wherein the treatment information includes information related to a physician who performs the catheter treatment, information related to a treatment device used for the catheter treatment, or information related to a technique of the catheter treatment.

10. The information processing device according to claim 6, wherein the processor is configured to:

obtain a captured image of an inside of a catheter room obtained by capturing an execution status of the catheter treatment that is being performed on the patient;

specify work contents of a physician performing the catheter treatment based on the captured image of the inside of the catheter room; and obtain the execution treatment information including the required time of each completed procedure based on the specified work contents of the physician performing the catheter treatment based on the captured image of the inside of the catheter room.

11. The non-transitory computer-readable medium according to claim 1, further comprising:

presenting an execution schedule of each subsequent procedure related to the catheter treatment that is being performed on the patient.

12. The non-transitory computer-readable medium according to claim 1, further comprising:

predicting a scheduled end time of the catheter treatment that is being performed on the patient; and scheduling catheter treatments to be performed after the scheduled end time of the catheter treatment that is being performed on the patient.

13. The non-transitory computer-readable medium according to claim 5, further comprising:

obtaining the captured image of the inside of the catheter room with a camera.

14. The information processing device according to claim 10, further comprising:

a camera configured to obtain the captured image of the inside of the catheter room.

15. The non-transitory computer-readable medium according to claim 1, wherein the reservation screen displays the use status of one or more catheter rooms indicated by different hatching for accepted time zones and unoccupied times zones beneath a patient identifier, treatment information of a treatment target patient, a predicted treatment time and fee, and a schedule of person in charge on an execution scheduled day, the schedule of person in charge being displayed in a plurality of time zones, which are indicated by different hatching for a time in which the catheter treatment can be performed and a time in which the catheter treatment cannot be performed.

* * * * *